US009722189B2

(12) United States Patent
Tada

(10) Patent No.: US 9,722,189 B2
(45) Date of Patent: Aug. 1, 2017

(54) ADAMANTANE COMPOUND FOR ORGANIC ELECTROLUMINESCENT ELEMENTS, AND ORGANIC ELECTROLUMINESCENT ELEMENT

(71) Applicant: NIPPON STEEL & SUMIKIN CHEMICAL CO., LTD., Tokyo (JP)

(72) Inventor: Masashi Tada, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 105 days.

(21) Appl. No.: 14/783,797

(22) PCT Filed: Apr. 8, 2014

(86) PCT No.: PCT/JP2014/060174
§ 371 (c)(1),
(2) Date: Oct. 9, 2015

(87) PCT Pub. No.: WO2014/168138
PCT Pub. Date: Oct. 16, 2014

(65) Prior Publication Data
US 2016/0072064 A1 Mar. 10, 2016

(30) Foreign Application Priority Data
Apr. 11, 2013 (JP) ................................ 2013-082813

(51) Int. Cl.
H01L 51/50 (2006.01)
H01L 51/00 (2006.01)
(Continued)

(52) U.S. Cl.
CPC ............ *H01L 51/008* (2013.01); *C07F 5/027* (2013.01); *C09K 11/02* (2013.01); *C09K 11/06* (2013.01);
(Continued)

(58) Field of Classification Search
None
See application file for complete search history.

(56) References Cited

FOREIGN PATENT DOCUMENTS

JP    2000-290645 A    10/2000
JP    2003-31368 A    1/2003
(Continued)

OTHER PUBLICATIONS

Zou et al., N-Heterocyclci Carbene-Assisted, Bis(phosphine)nickel-Catalyzed Cross-Coupling of Diarylborinic Acides with Aryl Chlorides, Tosylates, and Sulfamates, 2014, Journal of Organic Chem. 79, pp. 7132-7140.*
(Continued)

*Primary Examiner* — Gregory Clark
(74) *Attorney, Agent, or Firm* — Cheng Law Group, PLLC

(57) ABSTRACT

Provided are an organic EL device practically satisfactory in terms of its light-emitting characteristics, driving voltage, and durability, and a compound for an organic EL device to be used in the device. The organic EL device has a structure in which an anode, a plurality of organic layers including a light-emitting layer, and a cathode are laminated on a substrate, and the organic EL device contains, in at least one organic layer selected from the light-emitting layer, a hole-transporting layer, an electron-transporting layer, a hole-blocking layer, and an electron-blocking layer, an adamantane compound having at least one triarylborane structure in a molecule thereof as the compound for an organic EL device.

11 Claims, 3 Drawing Sheets

(51) Int. Cl.
*C09K 11/06* (2006.01)
*C07F 5/02* (2006.01)
*C09K 11/02* (2006.01)

(52) U.S. Cl.
CPC ...... *H01L 51/0059* (2013.01); *H01L 51/0072* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/185* (2013.01); *H01L 51/5012* (2013.01); *H01L 51/5016* (2013.01)

(56) References Cited

FOREIGN PATENT DOCUMENTS

| | | |
|---|---|---|
| JP | 2005-317314 A | 11/2005 |
| JP | 2007-77064 A | 3/2007 |
| JP | 2011-93825 A | 5/2011 |
| WO | WO-03/080761 A1 | 10/2003 |
| WO | WO-2010/052932 A1 | 5/2010 |

OTHER PUBLICATIONS

International Search Report for the Application No. PCT/JP2014/060174 mailed Jul. 15, 2014.
English Translation of Written Opinion of the International Searching Authority (PCT/ISA/237) for Application No. PCT/JP2014/060174 dated Oct. 13, 2015.

\* cited by examiner

ADAMANTANE COMPOUND FOR ORGANIC ELECTROLUMINESCENT ELEMENTS, AND ORGANIC ELECTROLUMINESCENT ELEMENT

TECHNICAL FIELD

The present invention relates to a novel adamantane compound for an organic electroluminescent device and an organic electroluminescent device using the compound, and specifically, to a thin-film-type device that emits light when an electric field is applied to a light-emitting layer formed of an organic compound.

BACKGROUND ART

In general, an organic electroluminescent device (hereinafter referred to as organic EL device) is constructed of a light-emitting layer and a pair of counter electrodes interposing the light-emitting layer therebetween in its simplest structure. That is, the organic EL device uses the phenomenon that, when an electric field is applied between both the electrodes, electrons and holes are injected from a cathode and an anode, respectively, and each electron and each hole recombine in the light-emitting layer to emit light.

In recent years, progress has been made in developing an organic EL device using an organic thin film. In particular, development has been made in order to enhance luminous efficiency. In the development, the efficiency of injection of carriers from electrodes has been improved through optimization of the kind of the electrodes. In addition, there has been developed a device using a hole-transporting layer formed of an aromatic diamine and a light-emitting layer also serving as an electron-transporting layer formed of an 8-hydroxyquinoline aluminum complex (hereinafter referred to as Alq3), resulting in a significant improvement in luminous efficiency, as compared to related-art devices. Thus, the development of the organic EL device has been promoted in order to accomplish its practical application to a high-performance flat panel having features such as self-luminescence and rapid response.

Investigations have been made on using a phosphorescent light-emitting material rather than a fluorescent light-emitting material as an attempt to improve the luminous efficiency of a device. Many kinds of devices including the device in which a hole-transporting layer formed of an aromatic diamine and a light-emitting layer formed of Alq3 are formed emit light by using fluorescent light emission. However, by using phosphorescent light emission, that is, light emission from a triplet excited state, luminous efficiency is expected to be improved by from about three times to four times, as compared to the case of using the related-art devices in which fluorescent light emission (light emission from a singlet excited state) is used. In order to accomplish this purpose, investigations have been made on using a coumarin derivative or a benzophenone derivative in a light-emitting layer, but extremely low luminance has only been provided. Then, investigations have been made on using a europium complex as an attempt to use a triplet excited state, but highly efficient light emission has not been accomplished. As the investigations using phosphorescent light emission, many investigations have been made on using an iridium complex or the like as disclosed in Patent Literature 1 as a phosphorescent light-emitting dopant, and some materials having high luminous efficiency have been found.

CITATION LIST

Patent Literature

[PTL 1] WO 01/041512 A1
[PTL 2] JP 2001-313178 A
[PTL 3] JP 2002-352957 A
[PTL 4] WO 2010/052932 A1
[PTL 5] JP 2007-77064 A
[PTL 6] WO 03/080761 A1
[PTL 7] JP 2000-290645 A

As a host material to be used in the light-emitting layer of the organic EL device, there are given carbazole-based compounds disclosed in Patent Literatures 1 and 2, an oxazole-based compound and a triazole-based compound disclosed in Patent Literature 3, and the like. However, those compounds are not ones capable of standing practical use both in terms of efficiency and lifetime.

In addition, in Patent Literature 4, there is disclosed an adamantane compound having a triphenylsilyl group and a triarylamine structure as shown below.

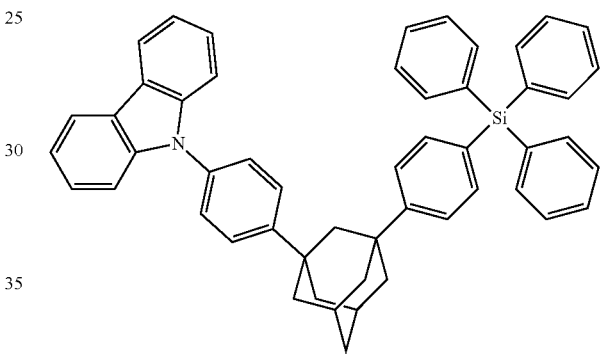

In Patent Literature 5, there is disclosed an arylamine compound obtained by substituting adamantane as shown below.

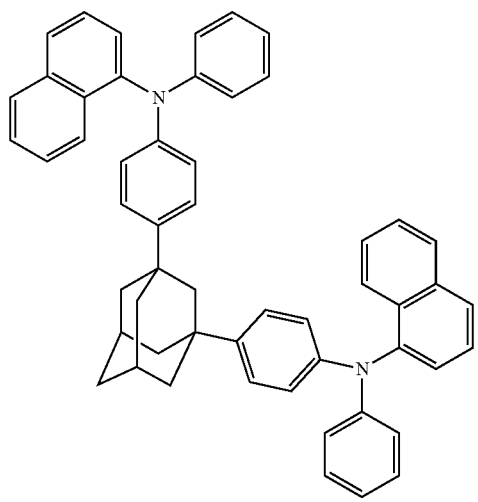 [SMILES: c1ccc(N(c2ccc(C34CC5CC(C3)CC(c3ccc(N(c6ccccc6)c6cccc7ccccc67)cc3)(C5)C4)cc2)c2cccc3ccccc23)cc1]

In Patent Literature 6, there is disclosed a carbazole compound obtained by substituting adamantane as shown below.

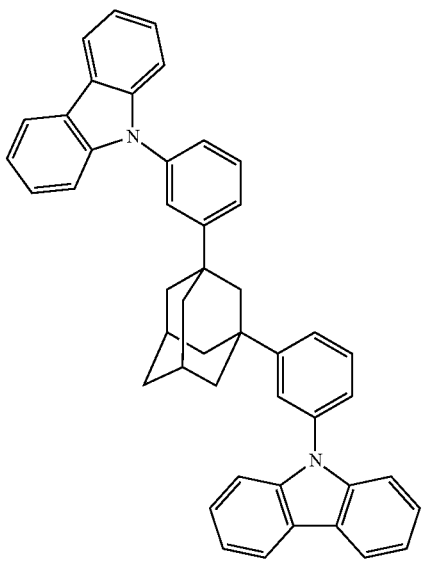 [SMILES: c1cc(-n2c3ccccc3c3ccccc32)cc(C23CC4CC(C2)CC(c2cccc(-n5c6ccccc6c6ccccc65)c2)(C4)C3)c1]

It should be noted that, with regard to a compound having a triarylborane structure, a compound as shown below is disclosed in Patent Literature 7. In addition, such compounds are also disclosed in WO 2008/152939 A1 and JP 2012-525378 A. However, those compounds do not have adamantane structures.

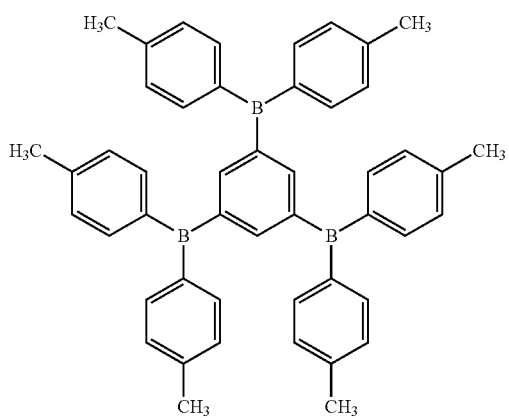

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device that has high luminous efficiency and high driving stability while having a low driving voltage, and is practically useful and a compound suitable for the organic EL device.

The inventors of the present invention have made intensive investigations and have consequently found that, when an adamantane compound having a triarylborane structure is used in an organic EL device, the organic EL device exhibits excellent characteristics. As a result, the present invention has been completed.

The present invention relates to a compound for an organic EL device, which is represented by the following general formula (1).

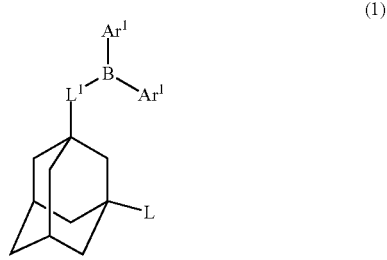

In the formula: L and $L^1$ each independently represent a monovalent or divalent group selected from a substituted or unsubstituted aromatic hydrocarbon group, a substituted or unsubstituted aromatic heterocyclic group, or a linked aromatic group formed by linking two to four of aromatic rings of the substituted or unsubstituted aromatic hydrocarbon groups and the substituted or unsubstituted aromatic heterocyclic groups, the linked aromatic group may be linear or branched, and the aromatic rings to be linked may be identical to or different from each other; and $Ar^1$'s each independently represent a substituted or unsubstituted aromatic hydrocarbon group or a substituted or unsubstituted aromatic heterocyclic group.

Preferred examples of the compound for an organic EL device include a compound represented by the following general formula (2) and a compound represented by the following general formula (3).

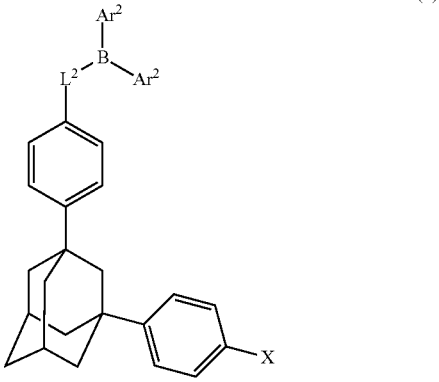

In the formula: $L^2$ represents a single bond or a divalent group selected from a substituted or unsubstituted aromatic hydrocarbon group, a substituted or unsubstituted aromatic heterocyclic group, or a linked aromatic group formed by linking two or three of aromatic rings of the substituted or unsubstituted aromatic hydrocarbon groups and the substituted or unsubstituted aromatic heterocyclic groups, the linked aromatic group may be linear or branched, and the aromatic rings to be linked may be identical to or different from each other; $Ar^2$'s each independently represent a substituted or unsubstituted aromatic hydrocarbon group or a substituted or unsubstituted aromatic heterocyclic group; and X represents hydrogen, a cyano group, an alkyl group, a diarylamino group, a triarylsilyl group, a diarylphosphinyl group, a diarylphosphine oxide group, a diarylboranyl group, a substituted or unsubstituted aromatic hydrocarbon group, or a substituted or unsubstituted aromatic heterocyclic group.

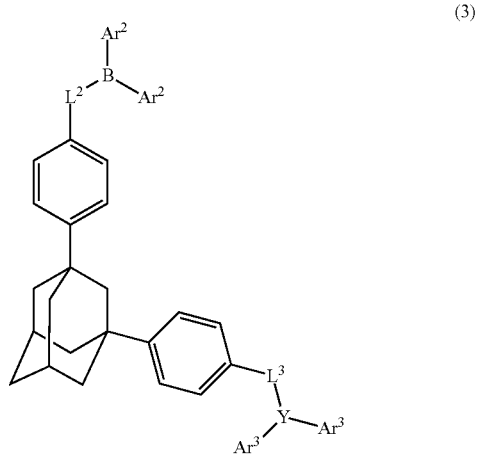

(3)

In the formula: L² and Ar² have the same meanings as L² and Ar² in the general formula (2), respectively; L³ represents a single bond or a divalent group selected from a substituted or unsubstituted aromatic hydrocarbon group, a substituted or unsubstituted aromatic heterocyclic group, or a linked aromatic group formed by linking two or three of aromatic rings of the substituted or unsubstituted aromatic hydrocarbon groups and the substituted or unsubstituted aromatic heterocyclic groups, the linked aromatic group may be linear or branched, and the aromatic rings to be linked may be identical to or different from each other; Y represents B, N, P, or P=O; and Ar³'s each independently represent a substituted or unsubstituted aromatic hydrocarbon group or a substituted or unsubstituted aromatic heterocyclic group, and two. Ar³'s may be bonded to each other to form a fused heterocycle.

The present invention also relates to an organic EL device including an organic layer containing the above-mentioned compound for an organic EL device. It is preferred that the organic layer be a light-emitting layer. It is more preferred that the organic EL device be one in which the light-emitting layer contains the compound for an organic EL device as a dopant, or the organic EL device be one in which the light-emitting layer contains a phosphorescent light-emitting dopant and the compound for an organic EL device as a host material.

The compound for an organic EL device of the present invention has excellent electrical characteristics and excellent electron-transporting characteristics, and is useful as a hole-transporting material, an electron-blocking material, a light-emitting material, a hole-blocking material, and an electron-transporting material of an organic EL device. The reason for this is considered to be the fact that its triarylborane skeleton has features of having a low lowest unoccupied molecular orbital (LUMO) energy level by virtue of conjugation extending through an unoccupied p orbital on boron, and further having high stability to electrochemical reduction. Further, the highest occupied molecular orbital (HOMO) energy level of the compound can be adjusted depending on an application by introducing various substituents in the compound through adamantane while its LUMO energy level is maintained at a low level.

Because of the foregoing, the organic EL device using the compound can realize a carrier balance optimum for enhancing luminous efficiency. As a result, the organic EL device having high luminous efficiency, a low driving voltage, and high durability can be provided.

DESCRIPTION OF EMBODIMENTS

Figure 1:
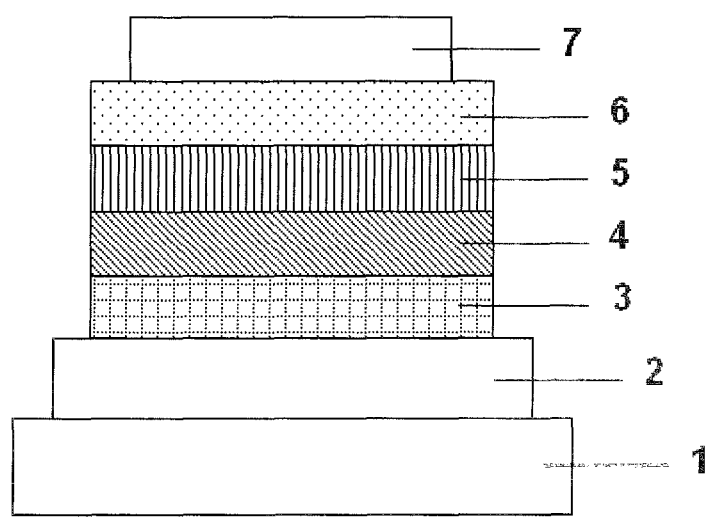
FIG. 1 is a sectional view for illustrating a structure example of an organic EL device.

A compound for an organic EL device of the present invention is represented by the general formula (1).

In the general formula (1), L and L¹ each independently represent a substituted or unsubstituted aromatic hydrocarbon group, a substituted or unsubstituted aromatic heterocyclic group, or a linked aromatic group formed by linking two to four of aromatic rings of the substituted or unsubstituted aromatic hydrocarbon groups and the substituted or unsubstituted aromatic heterocyclic groups. L represents a monovalent group, and L¹ represents a divalent group.

The simple expressions "aromatic hydrocarbon group" and "aromatic heterocyclic group" mean a substituted or unsubstituted aromatic hydrocarbon group and a substituted or unsubstituted aromatic heterocyclic group, respectively, unless otherwise stated. In addition, the simple expression "linked aromatic group" means a substituted or unsubstituted linked aromatic group, unless otherwise stated.

It should be noted that, when a group other than the aromatic hydrocarbon group and the aromatic heterocyclic group, such as an alkyl group or an arylamino group, has a hydrogen atom that can be substituted, even such group may have a substituent that can generally substitute the hydrogen atom.

The aromatic hydrocarbon group preferably has 6 to 30 carbon atoms, and the aromatic heterocyclic group preferably has 3 to 30 carbon atoms. When the aromatic hydrocarbon group and the aromatic heterocyclic group have substituents, the number of carbon atoms is calculated including the number of carbon atoms of the substituent.

The linked aromatic group is a linked aromatic group formed by linking two to four of aromatic rings of the aromatic hydrocarbon groups, the aromatic heterocyclic groups, or both of the aromatic hydrocarbon groups and the aromatic heterocyclic groups, preferably a linked aromatic group formed by linking two to four of aromatic rings of the aromatic hydrocarbon groups and the aromatic heterocyclic groups. The linked aromatic group may be linear or branched, and the aromatic rings to be linked may be identical to or different from each other. The linked aromatic group preferably has 6 to 80 carbon atoms. When the linked aromatic group has a substituent, the number of carbon atoms is calculated including the number of carbon atoms of the substituent. In addition, the "aromatic ring" is understood as having a meaning including an aromatic hydrocarbon ring, an aromatic heterocycle, or both of them.

Specific examples of the case where L and L¹ each represent an unsubstituted aromatic hydrocarbon group, aromatic heterocyclic group, or linked aromatic group include: a group produced by removing one or two hydrogen atoms from an aromatic compound, such as benzene, pentalene, indene, naphthalene, anthracene, phenanthrene, pyrrole, imidazole, pyrazole, thiazole, thiophene, pyridine, pyrazine, pyrimidine, pyridazine, triazine, isoindole, indazole, purine, benzimidazole, indolizine, chromene, benzoxazole, isobenzofuran, quinolizine, isoquinoline, imidazole, naphthyridine, phthalazine, quinazoline, quinoxaline, cinnoline, quinoline, pteridine, perimidine, phenanthroline, phenanthridine, acridine, phenazine, phenothiazine, phenoxazine, phenazasiline, dibenzodioxin, carboline, indole, indoloindole, carbazole, furan, benzofuran, isobenzofuran, benzothiazole, oxanthrene, dibenzofuran, thiophene, thioxanthene, thianthrene, phenoxathiin, thionaphthene, isothianaphthene, thiophthene, thiophanthrene, or dibenzothiophene; and a linked aromatic group produced by removing one or two hydrogen atoms from an aromatic compound in which two to four of such groups are linked.

In the case where L represents an unsubstituted monovalent linked aromatic group, examples of the structure of the linked aromatic group include such structures as represented by the following formulae (4) to (6). It should be noted that, in the case where $L^1$ represents a divalent linked aromatic group, structures each produced by removing one hydrogen atom from any one of those structures are adopted.

  (4)

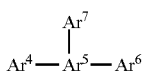  (5)

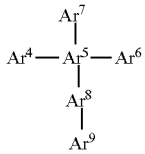  (6)

In the formulae (4) to (6), $Ar^4$ to $Ar^9$ each represent an unsubstituted monocyclic or fused aromatic ring, and may be identical to or different from one another.

As a substituent in the case where L and La each represent an aromatic hydrocarbon group having a substituent, an aromatic heterocyclic group having a substituent, or a linked aromatic group having a substituent, there are preferably given an alkyl group having 1 to 12 carbon atoms, an aralkyl group having 7 to 19 carbon atoms, an alkenyl group having 2 to 12 carbon atoms, an alkynyl group having 2 to 12 carbon atoms, a cyano group, a dialkylamino group having 2 to 24 carbon atoms, a diarylamino group having 6 to 36 carbon atoms, a diaralkylamino group having 14 to 38 carbon atoms, an amino group, a nitro group, an acyl group, an alkoxycarbonyl group having 2 to 12 carbon atoms, a carboxyl group, an alkoxyl group having 1 to 12 carbon atoms, an alkylsulfonyl group having 1 to 12 carbon atoms, a haloalkyl group having 1 to 12 carbon atoms, a hydroxyl group, an amide group, a phenoxy group, an alkylthio group having 1 to 12 carbon atoms, an alkoxycarbonyloxy group having 2 to 20 carbon atoms, a trialkylsilyl group having 3 to 40 carbon atoms, a triarylsilyl group having 18 to 36 carbon atoms, a dialkylphosphino group having 2 to 40 carbon atoms, a diarylphosphino group having 12 to 44 carbon atoms, a dialkylphosphine oxide group having 2 to 40 carbon atoms, a diarylphosphine oxide group having 12 to 44 carbon atoms, a dialkylboryl group having 2 to 40 carbon atoms, and a diarylboryl group having 12 to 44 carbon atoms. Of those, the following groups are more preferred: an alkyl group having 1 to 12 carbon atoms, an aralkyl group having 7 to 19 carbon atoms, an alkenyl group having 2 to 12 carbon atoms, an alkynyl group having 2 to 12 carbon atoms, a dialkylamino group having 2 to 24 carbon atoms, a diarylamino group having 6 to 36 carbon atoms, a diaralkylamino group having 14 to 38 carbon atoms, an acyl group having 2 to 12 carbon atoms, an alkoxycarbonyl group having 2 to 12 carbon atoms, an alkoxyl group having 1 to 12 carbon atoms, an alkylsulfonyl group having 1 to 12 carbon atoms, a haloalkyl group having 1 to 12 carbon atoms, a phenoxy group, an alkylthio group having 1 to 12 carbon atoms, a trialkylsilyl group having 3 to 40 carbon atoms, a triarylsilyl group having 18 to 36 carbon atoms, a dialkylphosphino group having 2 to 40 carbon atoms, a diarylphosphino group having 12 to 44 carbon atoms, a dialkylphosphine oxide group having 2 to 40 carbon atoms, a diarylphosphine oxide group having 12 to 44 carbon atoms, a dialkylboryl group having 2 to 40 carbon atoms, and a diarylboryl group having 12 to 44 carbon atoms.

$L^1$ preferably represents phenylene, and L preferably represents phenyl or substituted phenyl.

In the general formula (1), $Ar^1$'s each independently represent an aromatic hydrocarbon group or an aromatic heterocyclic group, preferably an aromatic hydrocarbon group having 6 to 30 carbon atoms or an aromatic heterocyclic group having 3 to 30 carbon atoms, more preferably an aromatic hydrocarbon group having 6 to 18 carbon atoms or an aromatic heterocyclic group having 3 to 17 carbon atoms. When the aromatic hydrocarbon group and the aromatic heterocyclic group have substituents, the number of carbon atoms is calculated including the number of carbon atoms of the substituent.

Examples of an unsubstituted aromatic hydrocarbon group and an unsubstituted aromatic heterocyclic group are the same as those described for L.

As a substituent in the case where $Ar^1$ represents an aromatic hydrocarbon group having a substituent or an aromatic heterocyclic group having a substituent, there are preferably given a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, a phenoxy group, an alkyl thio group having 1 to 20 carbon atoms, an aromatic hydrocarbon group having 6 to 30 carbon atoms, and an aromatic heterocyclic group having 3 to 30 carbon atoms. Of those, the following groups are more preferred: an alkyl group having 1 to 20 carbon atoms, an alkoxy group having 1 to 20 carbon atoms, a phenoxy group, an aromatic hydrocarbon group having 6 to 30 carbon atoms, and an aromatic heterocyclic group having 3 to 30 carbon atoms.

Of the compounds represented by the general formula (1), a preferred compound is a compound represented by the general formula (2) described above.

In the general formula (2), $L^2$ is understood as a group in which $L^1$ in the general formula (1) is changed to -Ph-$L^2$- (where Ph represents phenylene). That is, $L^2$ is understood as a group produced by removing, from $L^2$ in the case of having phenylene on its terminal, the phenylene. The range of $L^2$ is determined based on the fact just described and the description of $L^1$, but preferred examples of $L^2$ are as described below.

$L^2$ represents a single bond or a divalent group selected from an aromatic hydrocarbon group, an aromatic heterocyclic group, or a linked aromatic group formed by linking two or three of aromatic rings of the aromatic hydrocarbon groups and the aromatic heterocyclic groups. $L^2$ represents preferably a single bond, an aromatic hydrocarbon group having 6 to 24 carbon atoms, an aromatic heterocyclic group having 3 to 30 carbon atoms, or a linked aromatic group formed by linking two or three of aromatic rings of the aromatic hydrocarbon groups and the aromatic heterocyclic groups, more preferably a single bond, an aromatic hydrocarbon group having 6 to 18 carbon atoms, an aromatic heterocyclic group having 3 to 17 carbon atoms, or a linked aromatic group formed by linking two or three of aromatic rings of these groups. The linked aromatic group may be linear or branched, and the aromatic rings to be linked may be identical to or different from each other. When the aromatic hydrocarbon group and the aromatic heterocyclic group have substituents, the number of carbon atoms is calculated including the number of carbon atoms of the substituent.

Herein, the aromatic hydrocarbon group, the aromatic heterocyclic group, and the linked aromatic group are the same as the aromatic hydrocarbon group, the aromatic heterocyclic group, and the linked aromatic group described for $L^1$ in the general formula (1) except that the preferred numbers of carbon atoms are partially different. In the case where those groups have substituents, the same holds true for the substituents.

In the general formula (2), examples of $Ar^2$ are the same as those described for $Ar^1$ in the general formula (1).

In the general formula (2), X is understood as a group in which L in the general formula (1) is changed to -Ph-X. That is, X is understood as a group produced by removing, from L in the case of having Ph on its terminal, the Ph. The range of X is determined based on the fact just described and the description of L, but preferred examples of X are as described below.

X represents hydrogen, a cyano group, an alkyl group, a diarylamino group, a triarylsilyl group, a diarylphosphinyl group, a diarylphosphine oxide group, a diarylboranyl group, an aromatic hydrocarbon group, or an aromatic heterocyclic group, preferably hydrogen, a cyano group, an alkyl group having 1 to 12 carbon atoms, a diarylamino group having 6 to 36 carbon atoms, a triarylsilyl group having 18 to 36 carbon atoms, a diarylphosphinyl group having 12 to 44 carbon atoms, a diarylphosphine oxide group having 12 to 44 carbon atoms, a diarylboranyl group having 12 to 44 carbon atoms, an aromatic hydrocarbon group having 6 to 30 carbon atoms, or an aromatic heterocyclic group having 3 to 30 carbon atoms, more preferably a diarylamino group having 6 to 36 carbon atoms, a triarylsilyl group having 18 to 36 carbon atoms, a diarylphosphinyl group having 12 to 44 carbon atoms, a diarylphosphine oxide group having 12 to 44 carbon atoms, or a diarylboranyl group having 12 to 44 carbon atoms.

Herein, examples of the aromatic hydrocarbon group and the aromatic heterocyclic group are the same as those described for $Ar^1$ in the general formula (1). In the case where those groups have substituents, the same holds true for the substituents.

Of the compounds represented by the general formula (2), a preferred one is a compound represented by the general formula (3) described above.

In the general formula (3), $L^2$ and $Ar^2$ have the same meanings as $L^2$ and $Ar^2$ in the general formula (2), respectively. The compound represented by the general formula (3) is understood as a compound in which X in the general formula (2) is limited to $L^3Y(Ar^3)_2$.

In the general formula (3), $L^3$ represents a single bond or a divalent group selected from an aromatic hydrocarbon group, an aromatic heterocyclic group, or a linked aromatic group formed by linking two or three of aromatic rings of the aromatic hydrocarbon groups and the aromatic heterocyclic groups, preferably a single bond, an aromatic hydrocarbon group having 6 to 30 carbon atoms, an aromatic heterocyclic group having 3 to 30 carbon atoms, or a linked aromatic group formed by linking two or three of aromatic rings of these groups, more preferably a single bond, an aromatic hydrocarbon group having 6 to 18 carbon atoms, an aromatic heterocyclic group having 3 to 17 carbon atoms, or a linked aromatic group formed by linking two or three of aromatic rings of these groups.

Herein, examples of the aromatic hydrocarbon group, the aromatic heterocyclic group, and the linked aromatic group are the same as those described for $L^1$ in the general formula (1). In the case where those groups have substituents, the same holds true for the substituents.

In the general formula (3), Y represents B, N, P, or P=O.

In the general formula (3), $Ar^3$'s each independently represent an aromatic hydrocarbon group or an aromatic heterocyclic group, preferably an aromatic hydrocarbon group having 6 to 30 carbon atoms or an aromatic heterocyclic group having 3 to 30 carbon atoms, more preferably an aromatic hydrocarbon group having 6 to 18 carbon atoms or an aromatic heterocyclic group having 3 to 17 carbon atoms. Herein, examples of the aromatic hydrocarbon group and the aromatic heterocyclic group are the same as those described for $Ar^1$ in the general formula (1). In the case where those groups have substituents, the same holds true for the substituents. In addition, two $Ar^3$'s may be bonded to each other to form a fused heterocycle containing Y.

In the general formulae (1) to (3), part or the whole of hydrogen atoms may be substituted by deuterium.

The adamantane compound having a triarylborane skeleton of the present invention is a novel compound, and for example, the adamantane compound having a triarylborane skeleton may be synthesized as follows: as shown in the following reaction formula I, 1,3-dibromoadamantane and an aromatic compound are allowed to react with each other to synthesize a corresponding diaryladamantane, followed by halogenation, lithiation using butyllithium, and then a reaction with a diarylfluoroborane

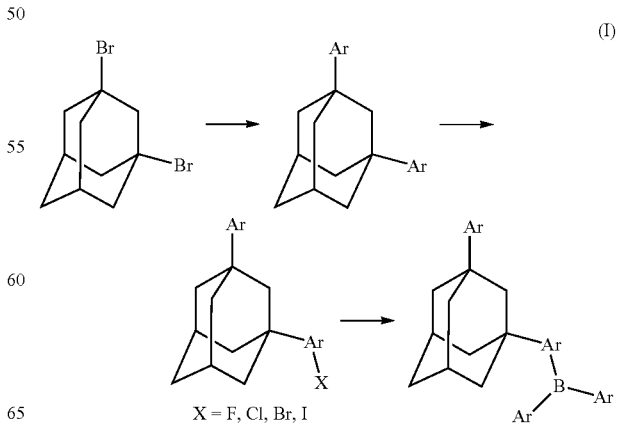

(I)

X = F, Cl, Br, I

Specific examples of the compounds represented by the general formulae (1) to (3) are shown below, but the compound for an organic electroluminescent device of the present invention is not limited thereto.
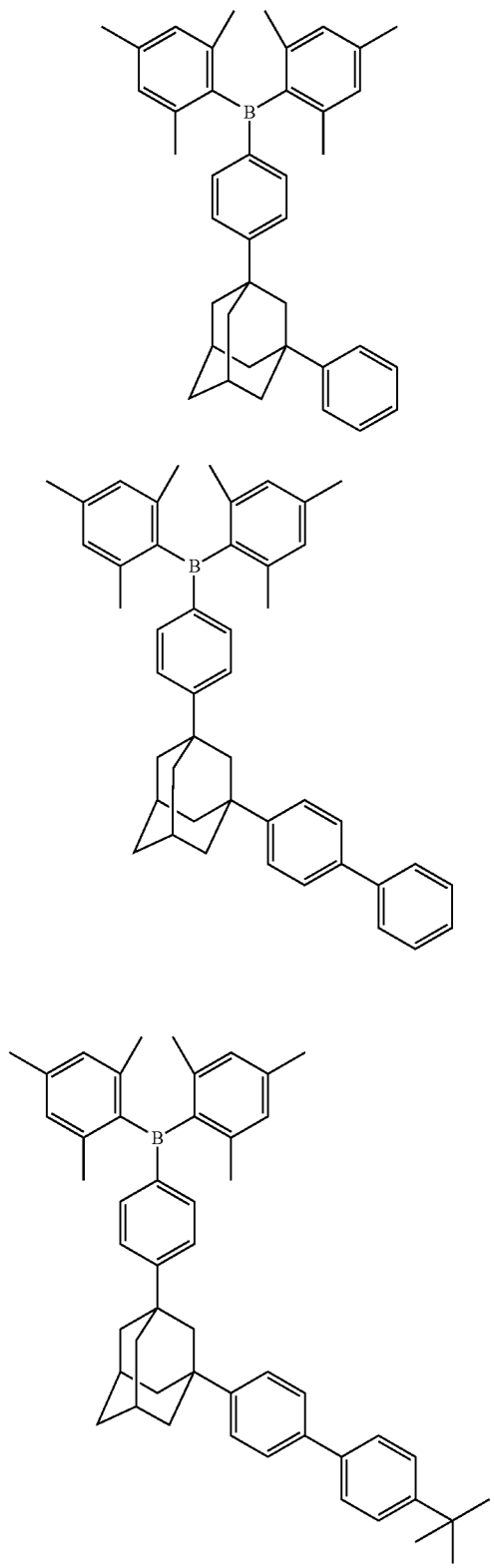
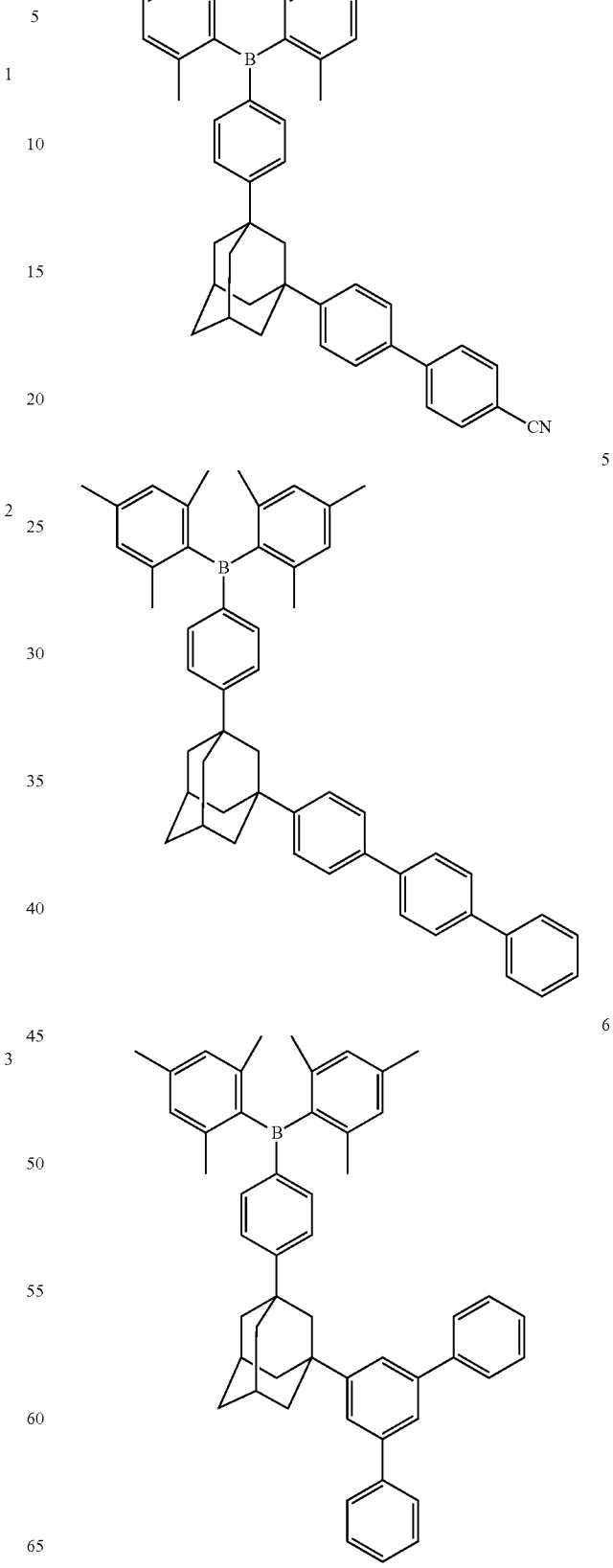

7
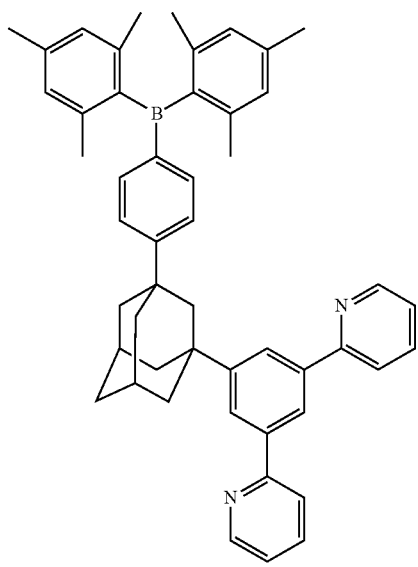
9
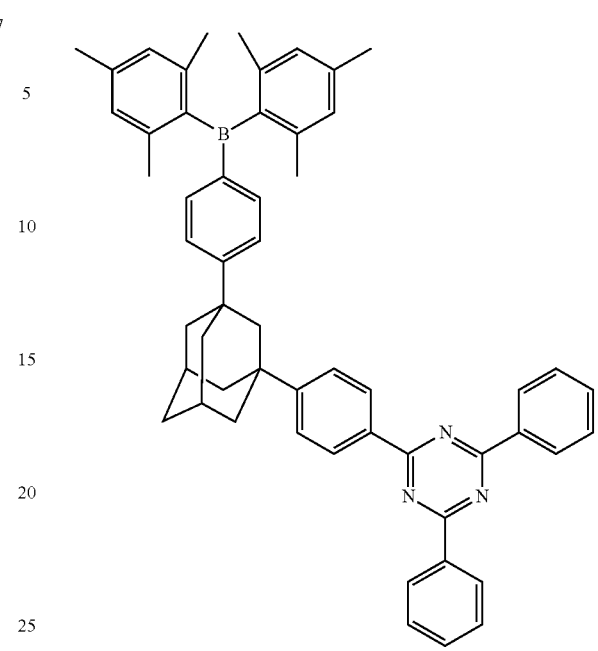
8
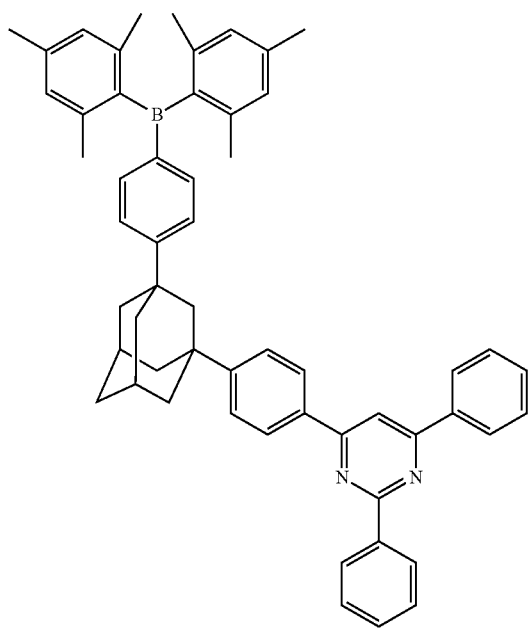
10
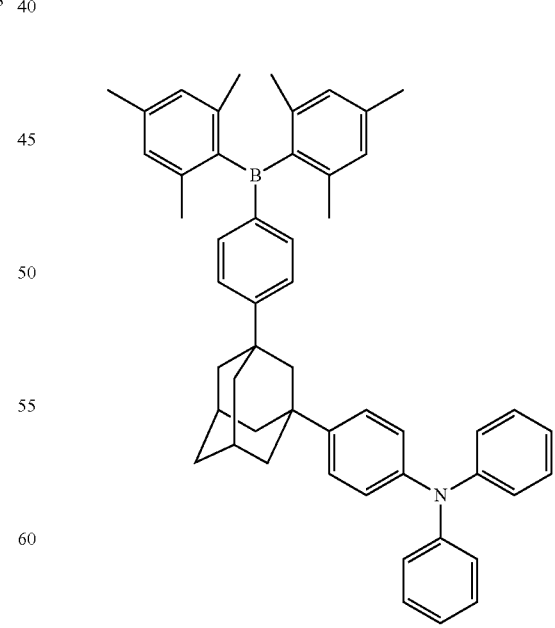

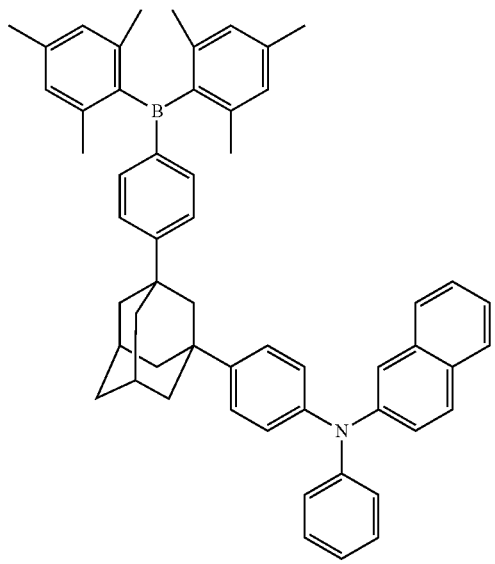
11
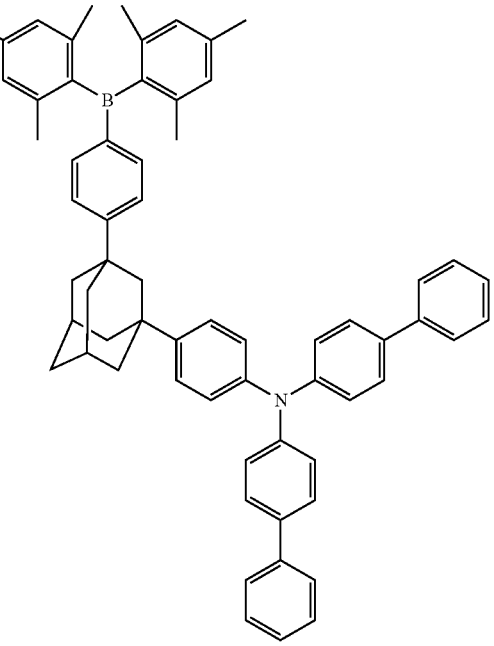
13
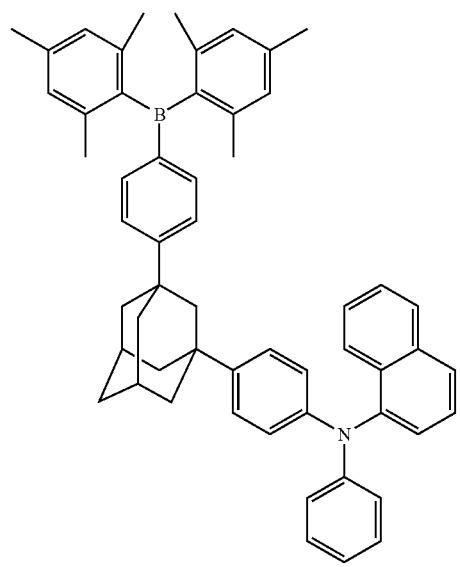
12
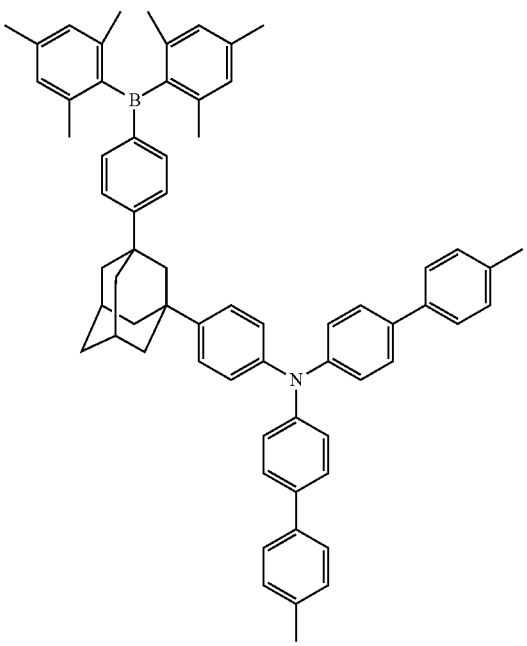
14

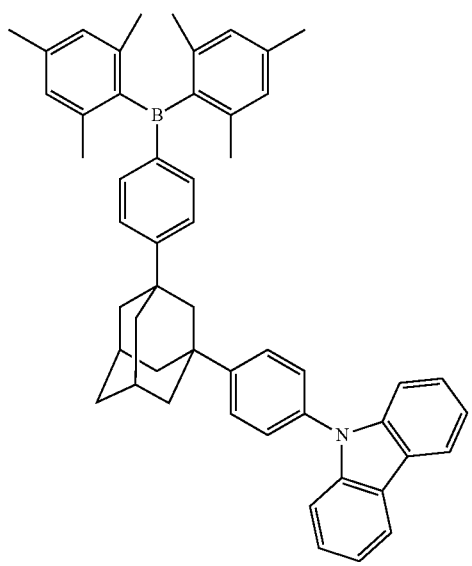
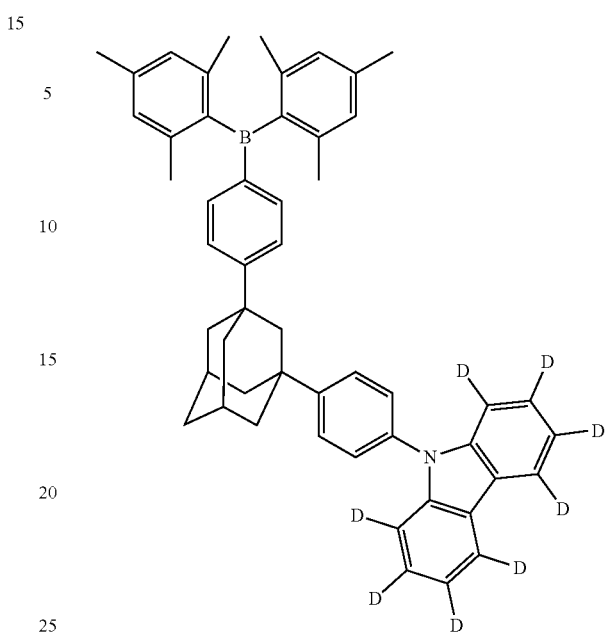

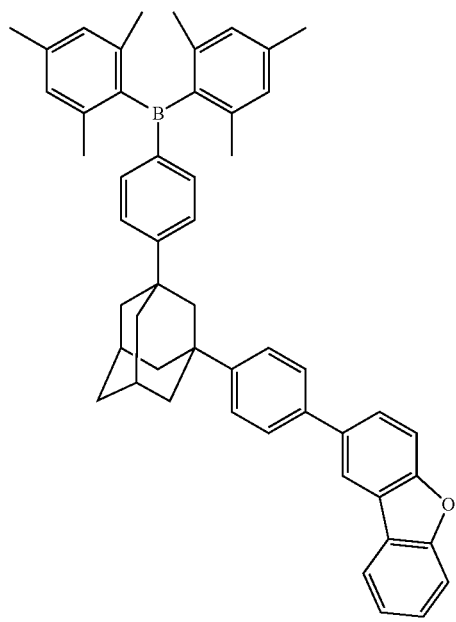
19
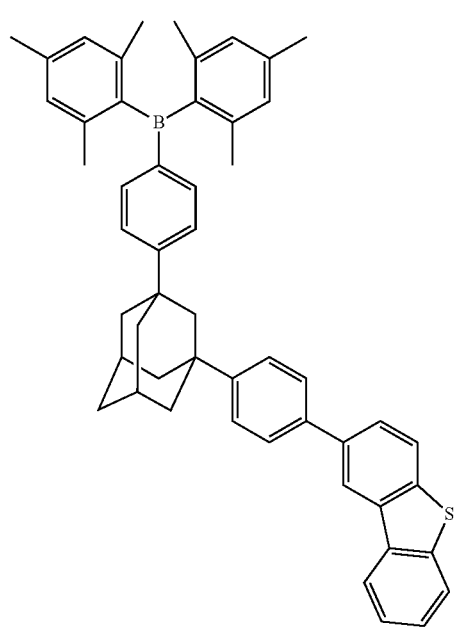
20
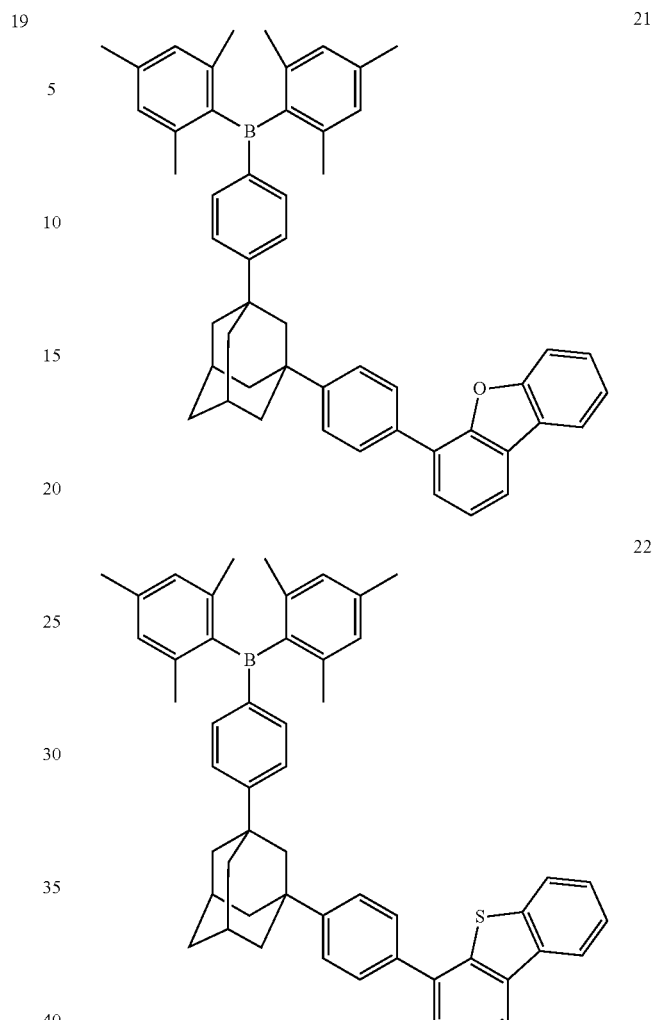
21
22
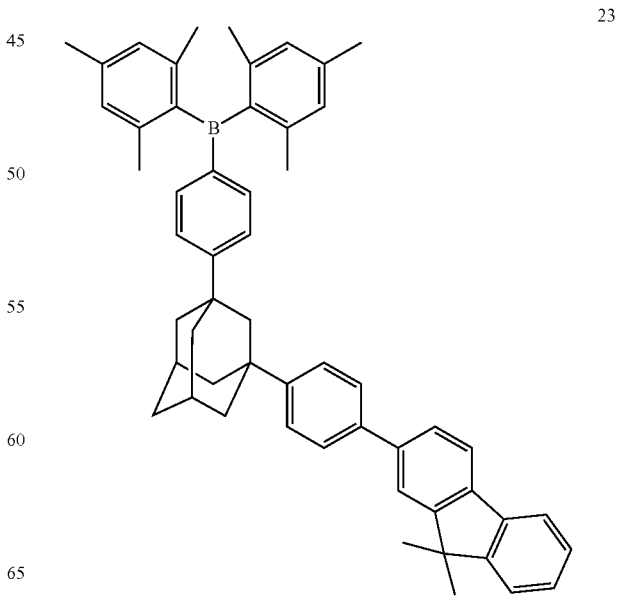
23

-continued
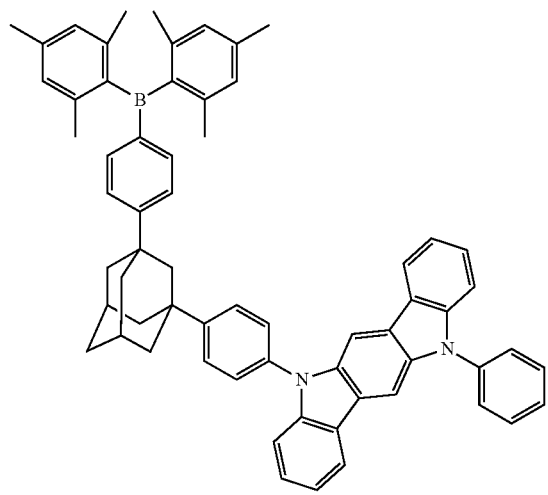
24
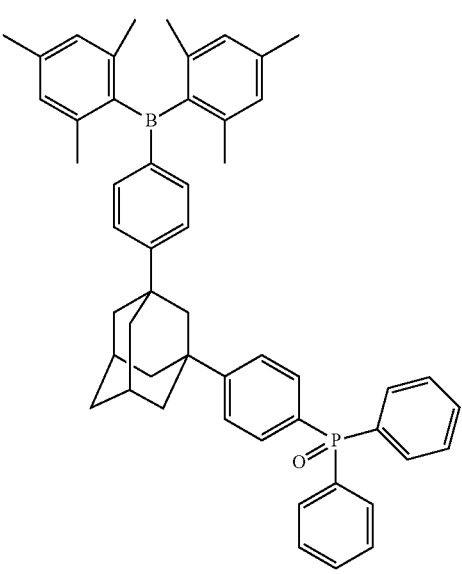
27
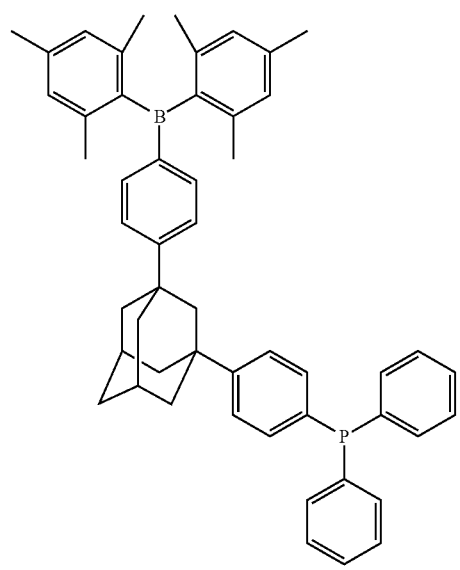
25
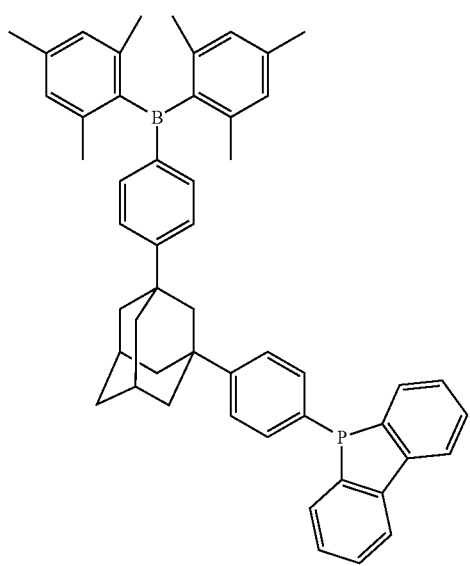
26
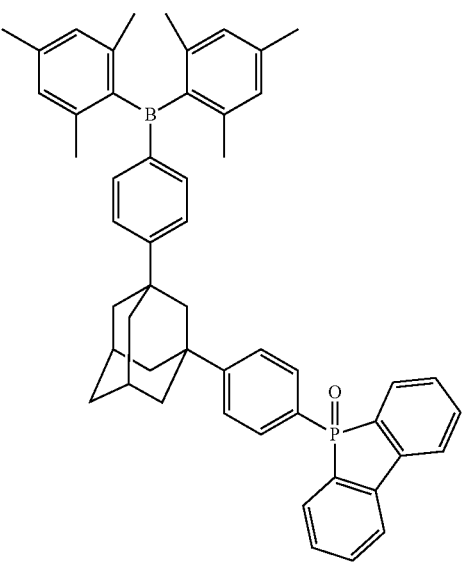
28

23
-continued
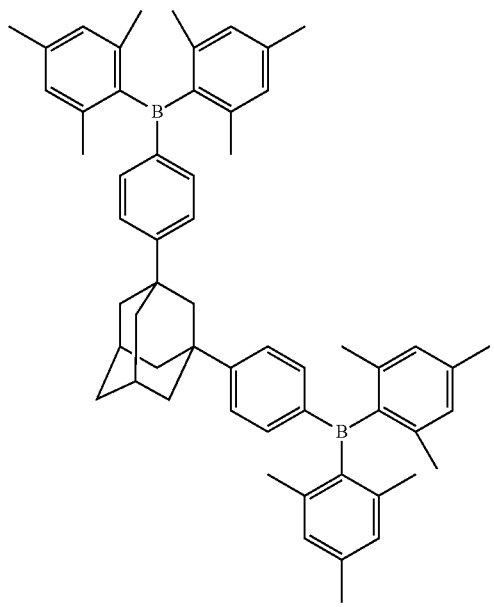
29
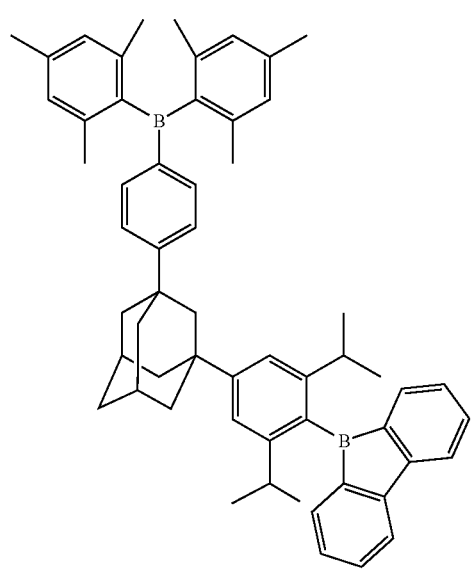
30
24
-continued
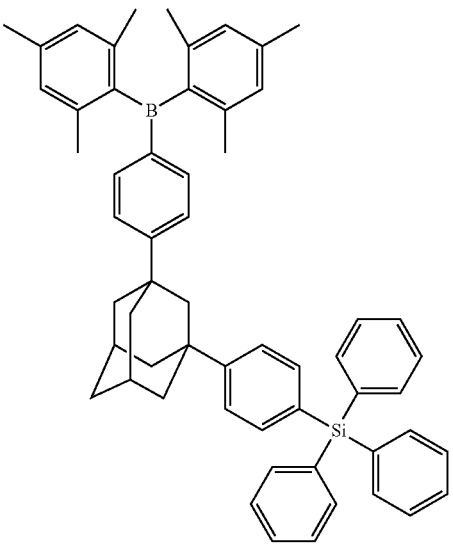
31
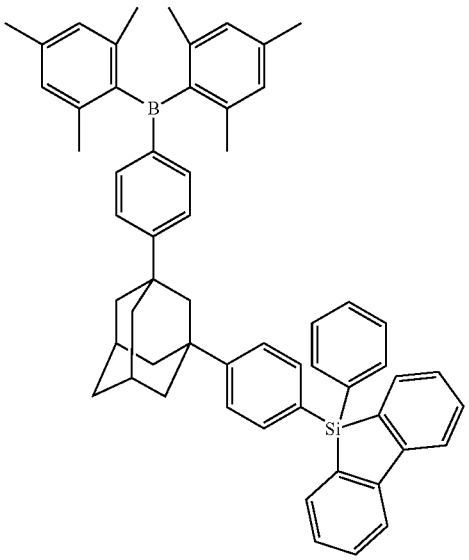
32
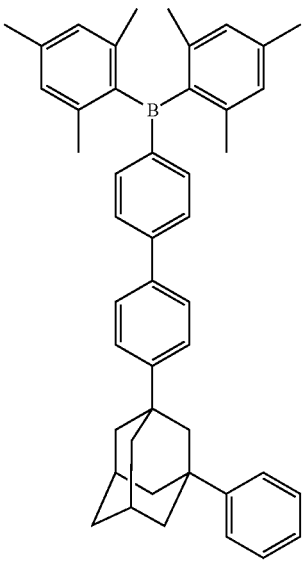
33

34
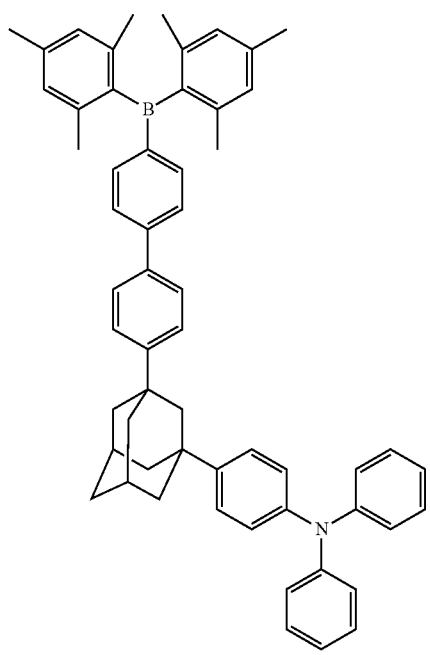
35
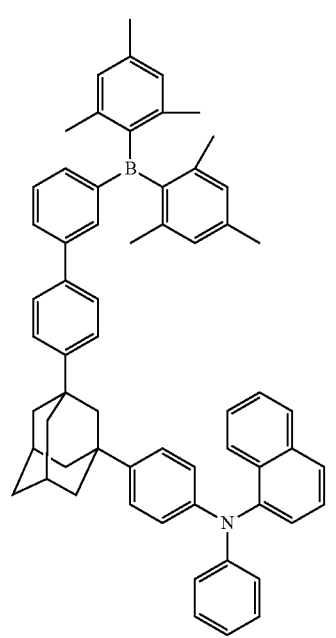
36
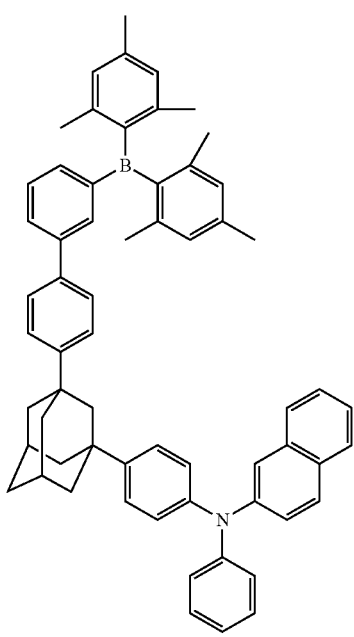
37
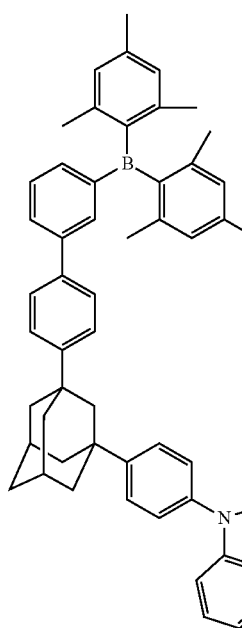

38
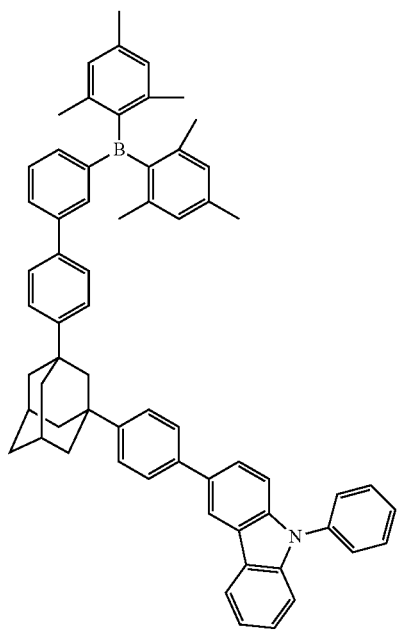
39
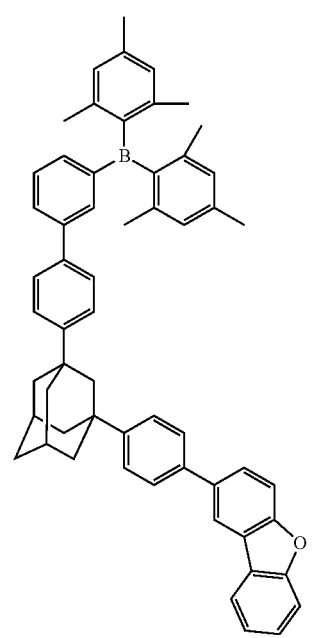
40
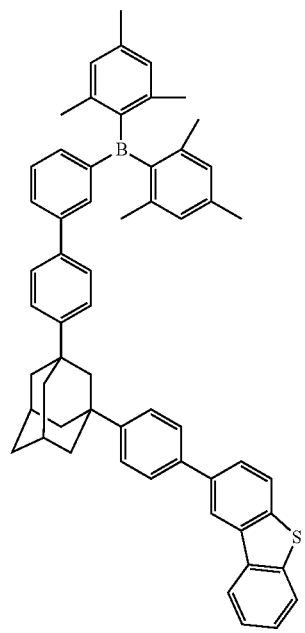
41
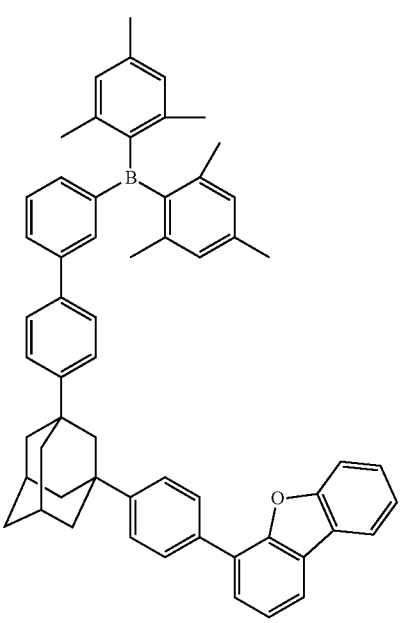

42
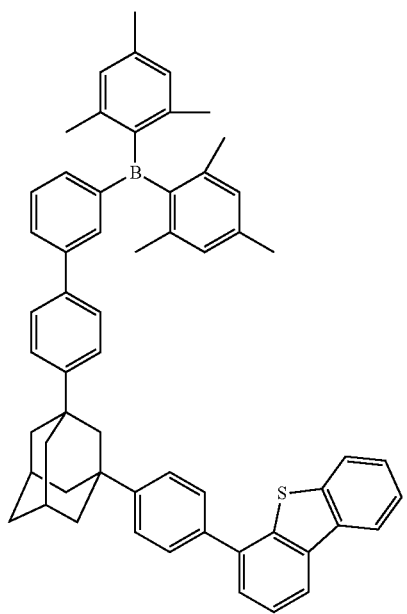
43
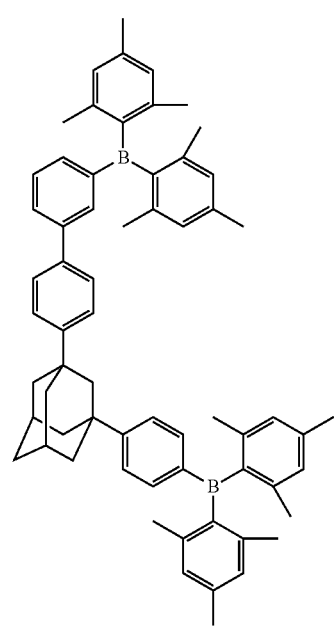
44
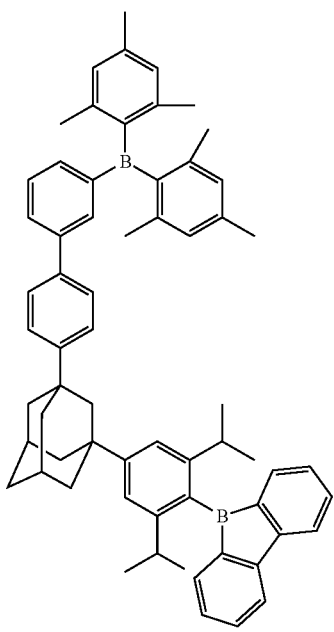
45
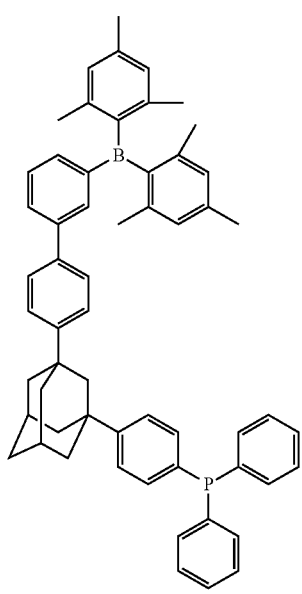

46
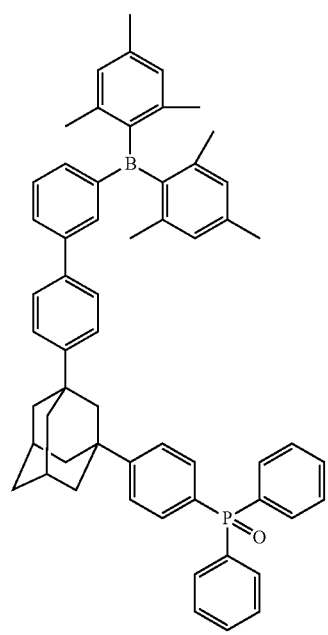
47
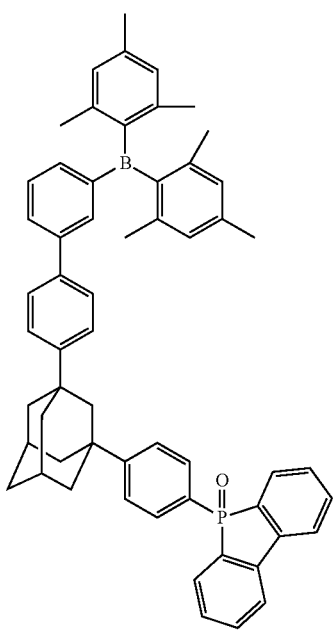
48
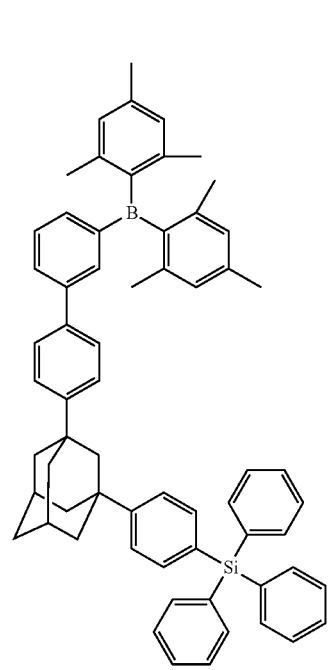
49

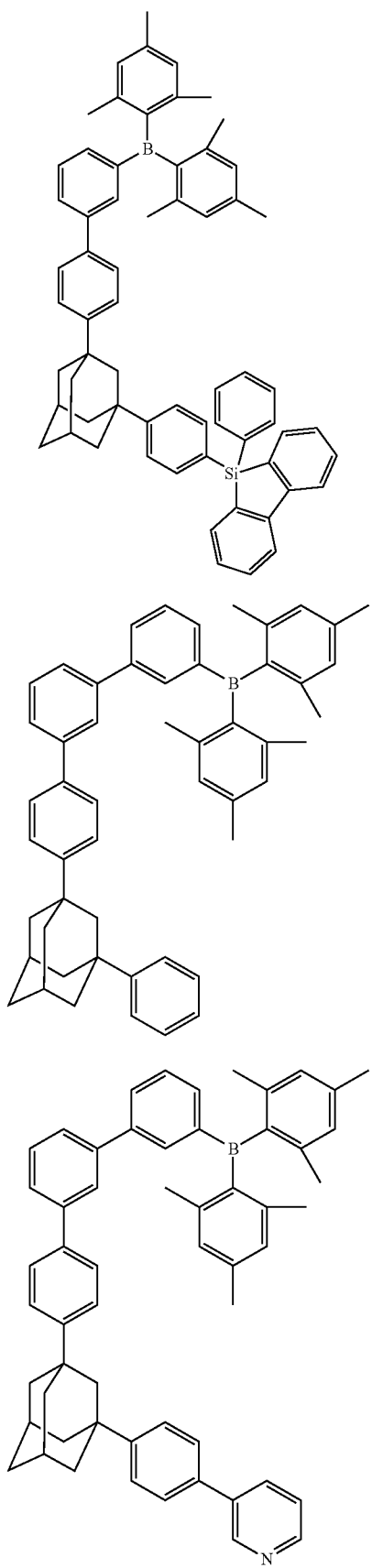
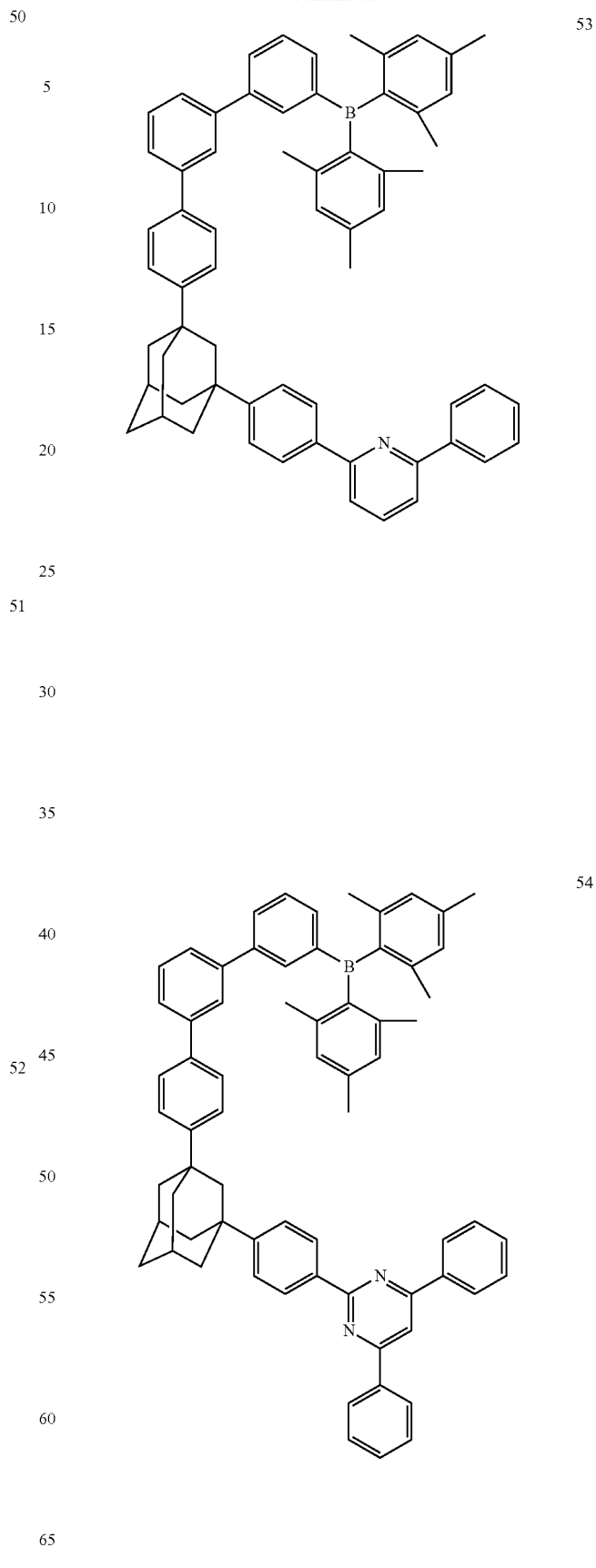

35
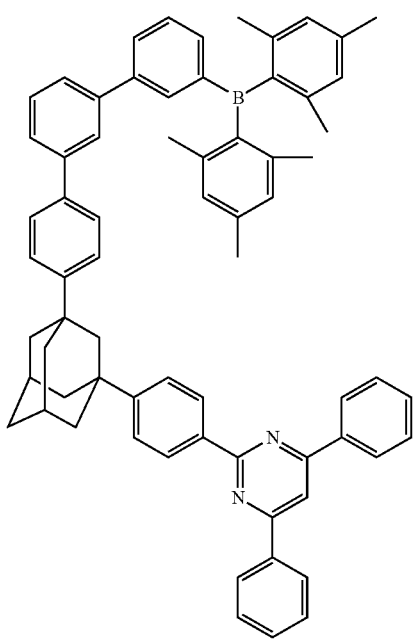
36
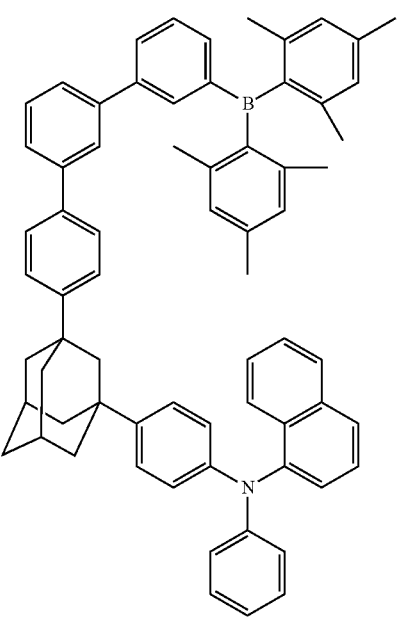
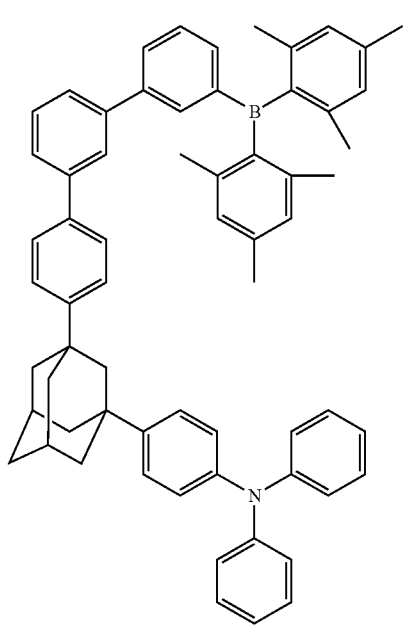
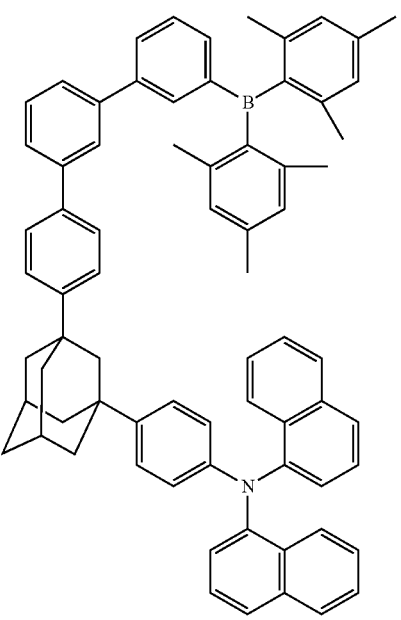

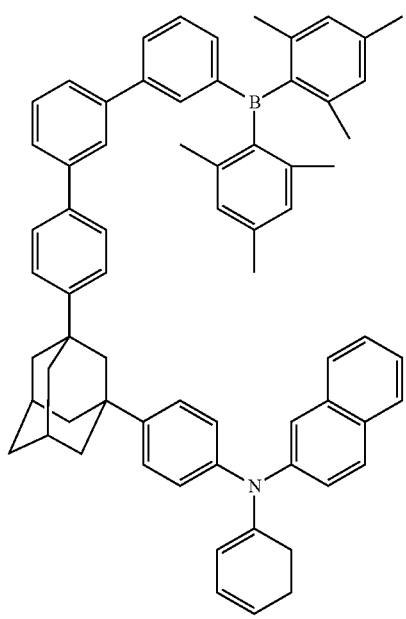
59
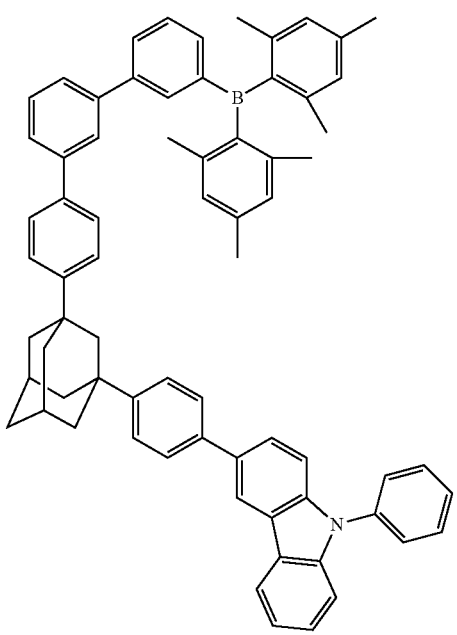
61
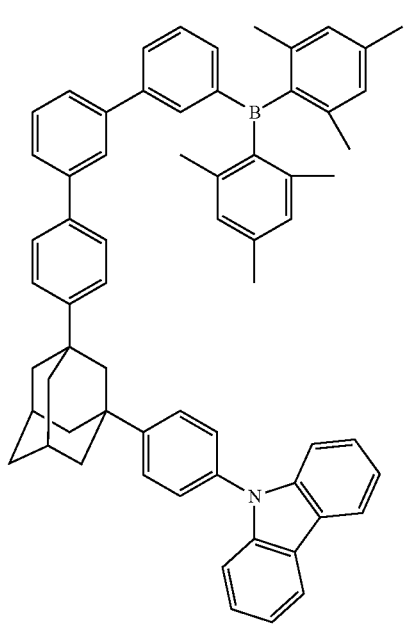
60
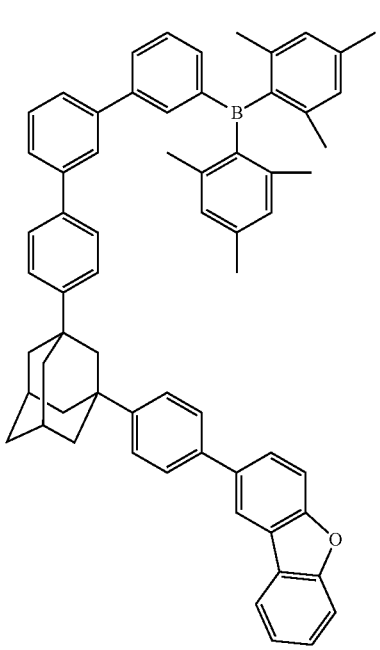
62

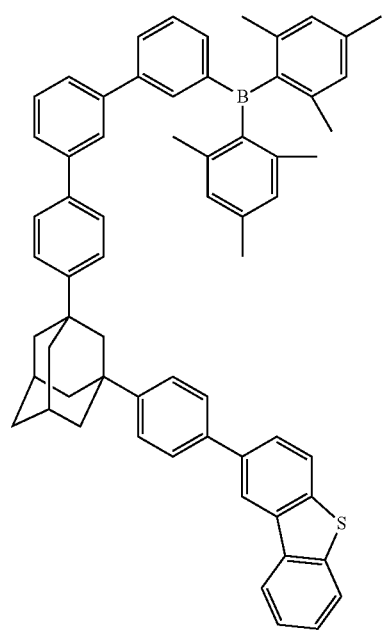
63
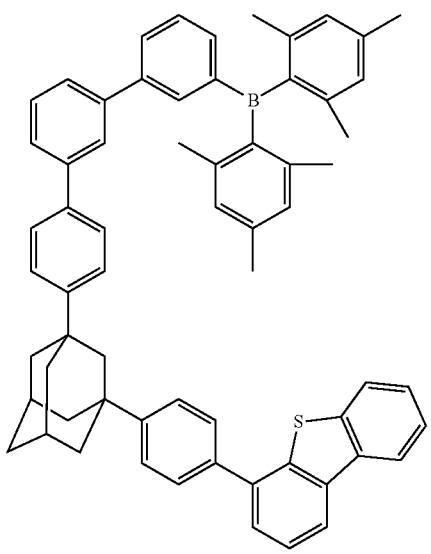
65
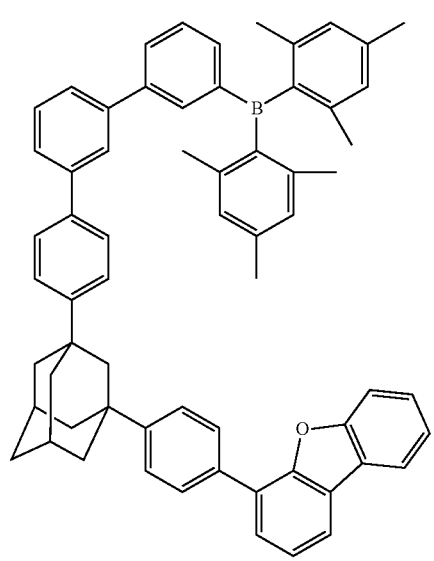
64
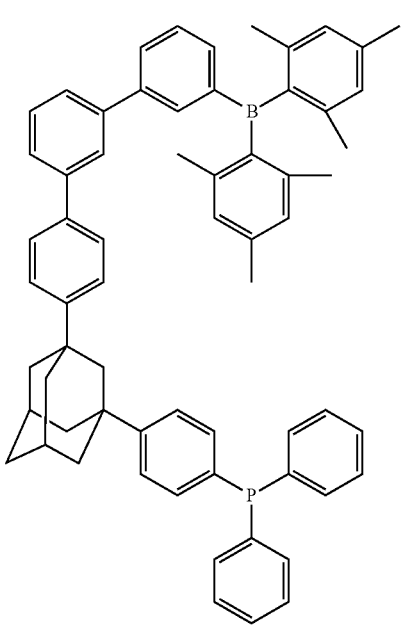
66

-continued
67
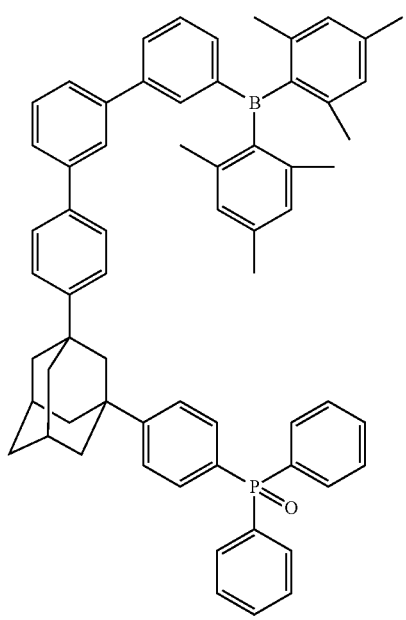
68
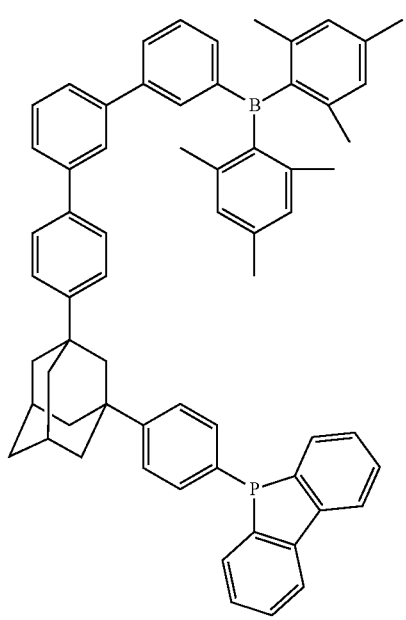
-continued
69
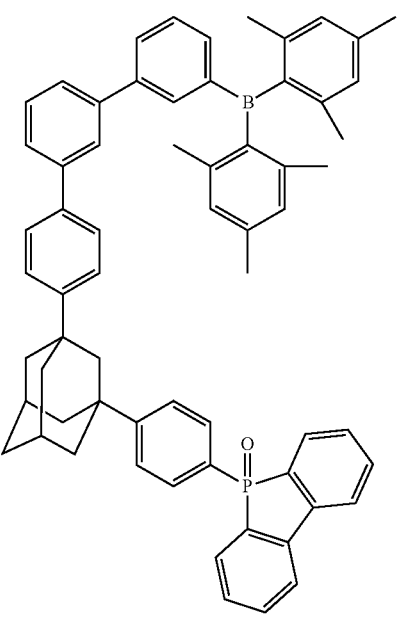
70
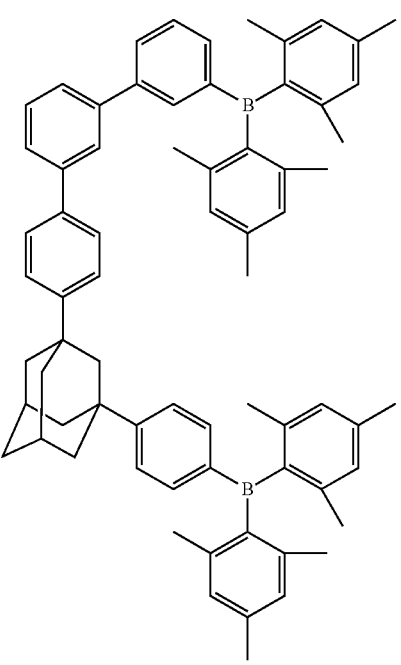

71
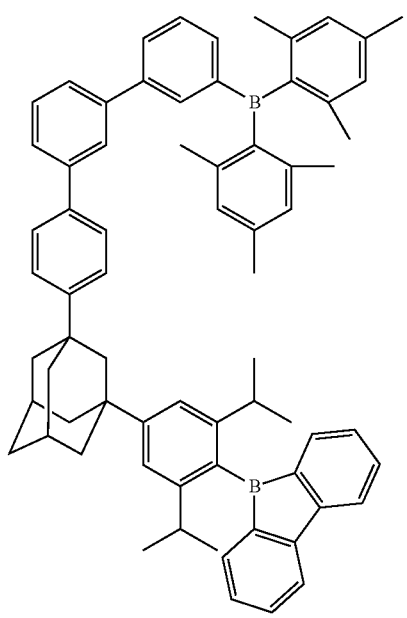
72
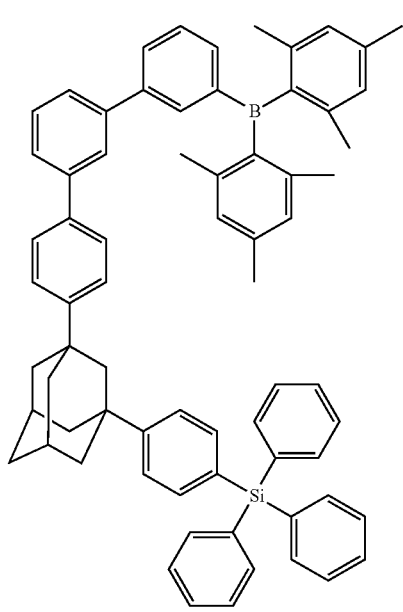
73
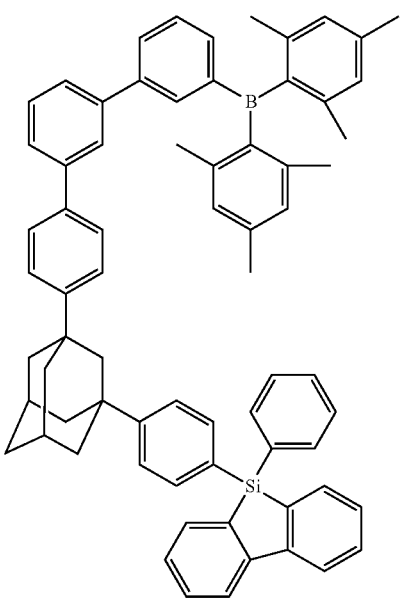
74
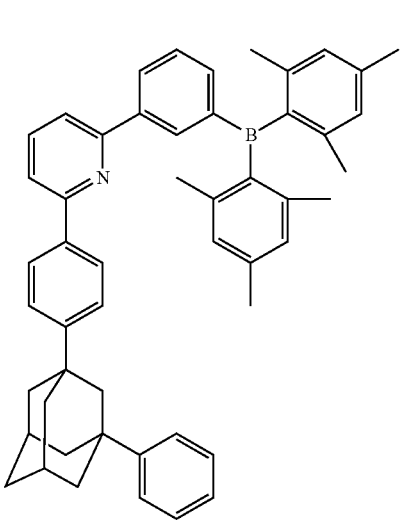

75
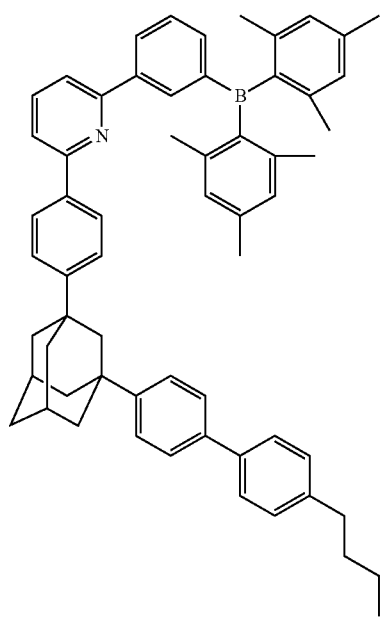
76
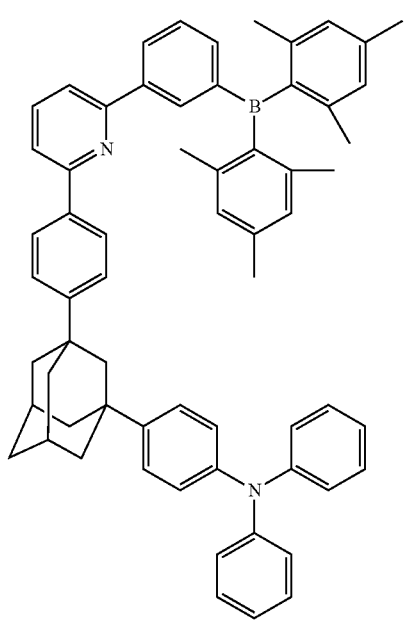
77
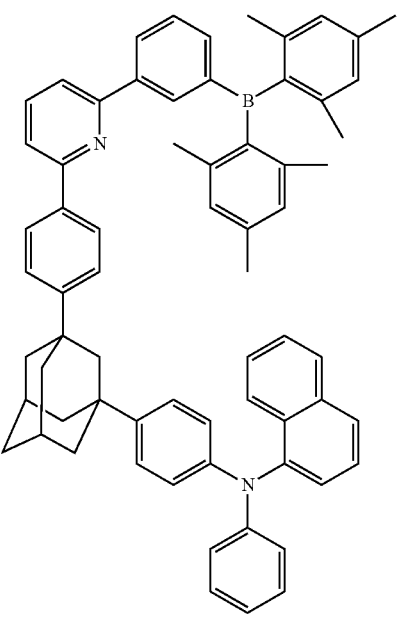
78
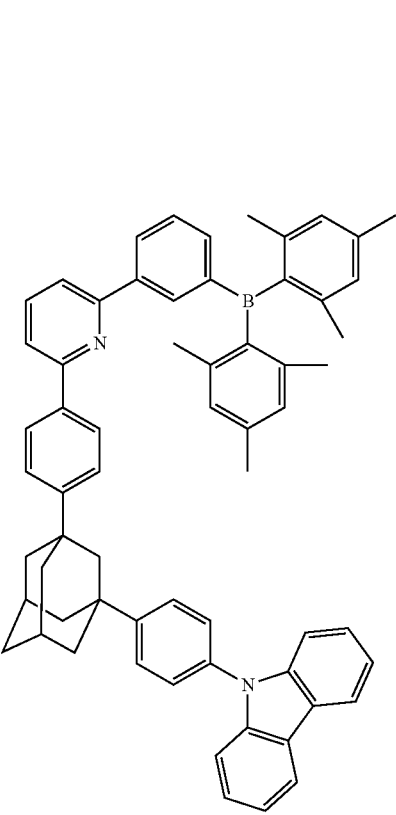

79
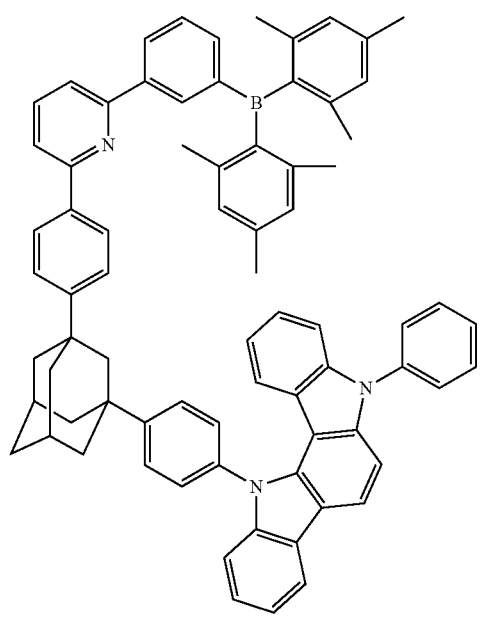
81
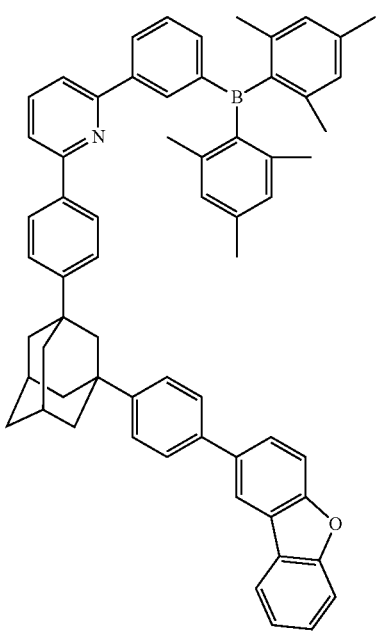
80
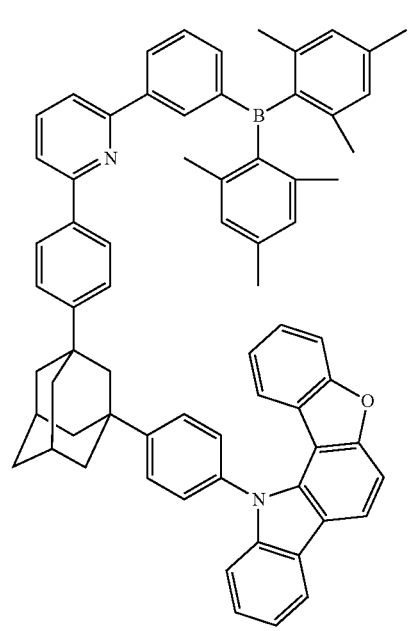
82
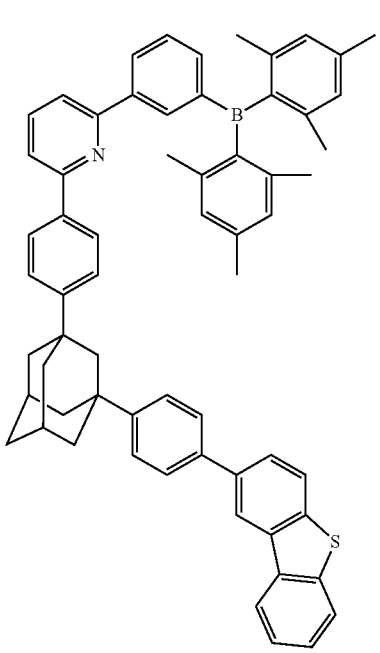

83
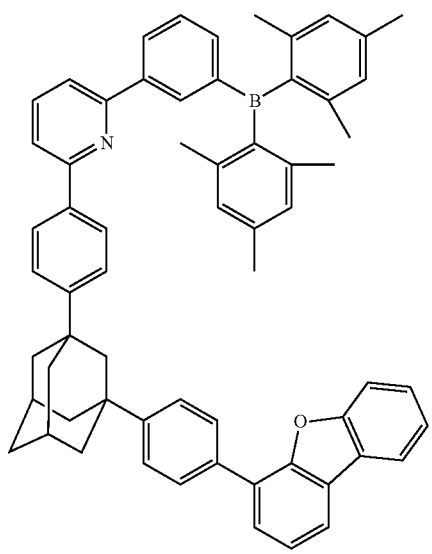
85
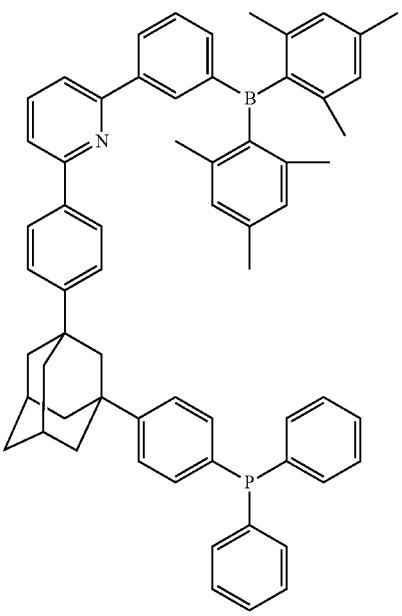
84
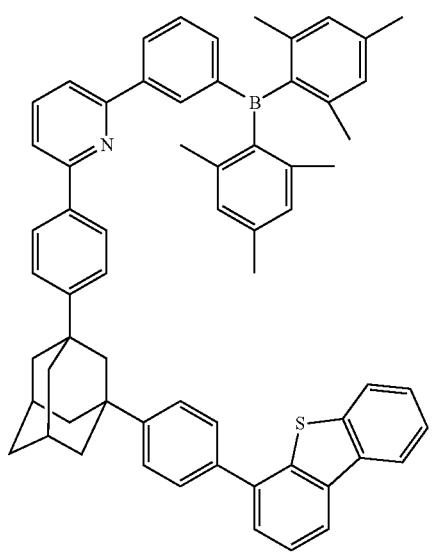
86
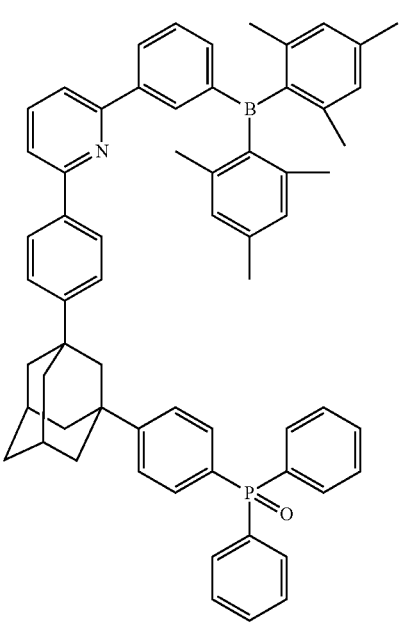

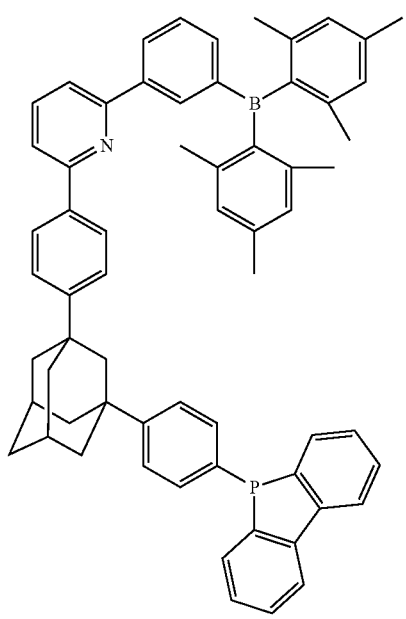
87
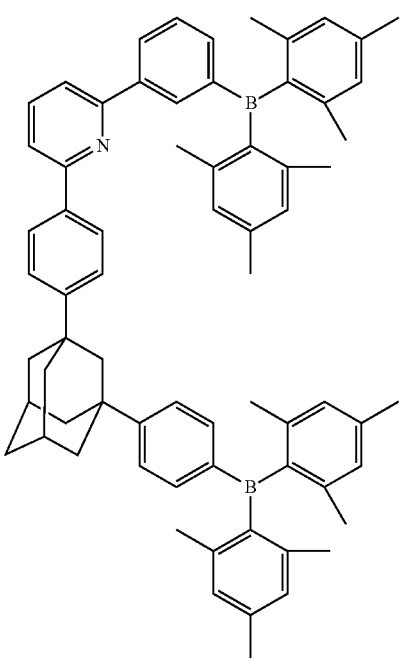
89
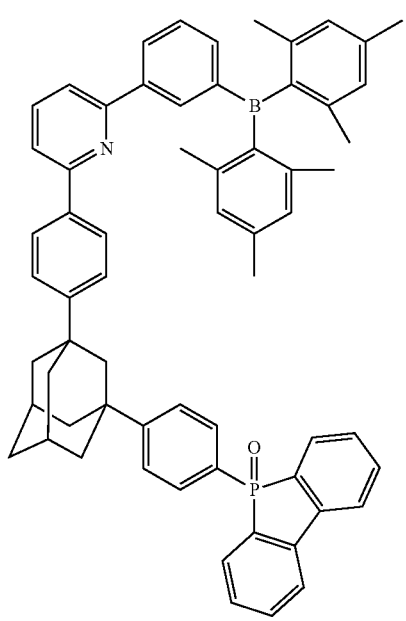
88
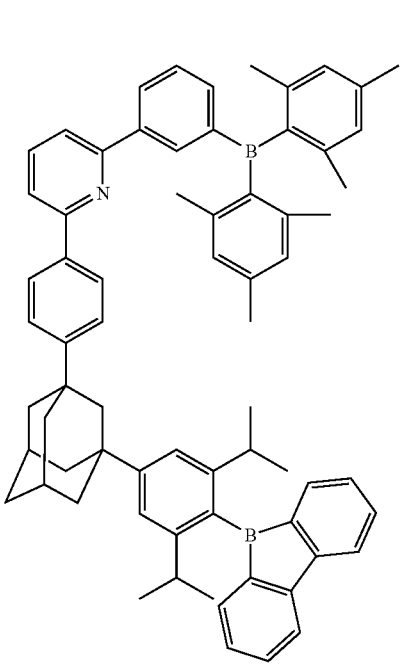
90

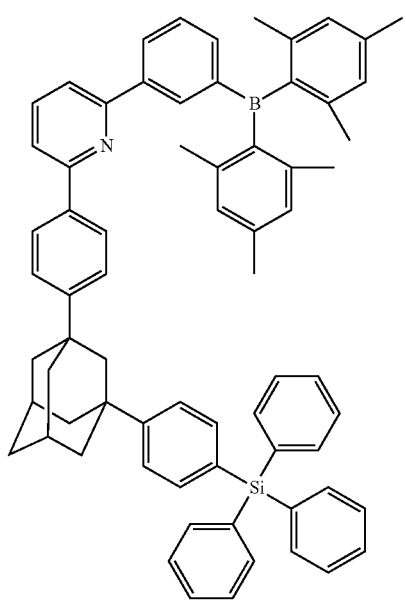
91
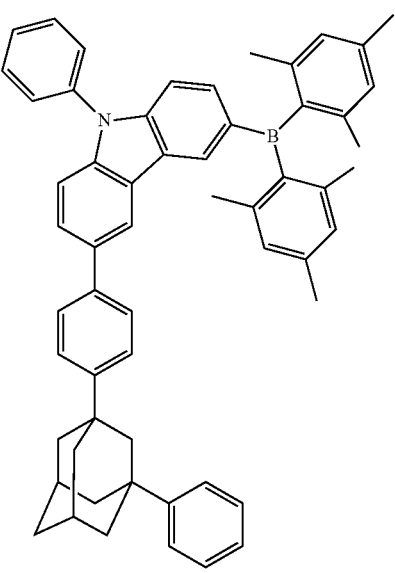
93
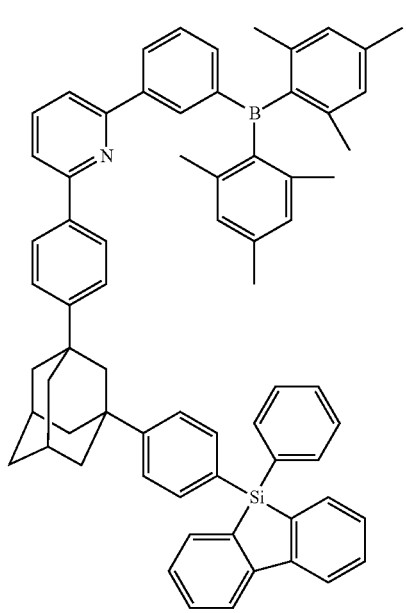
92
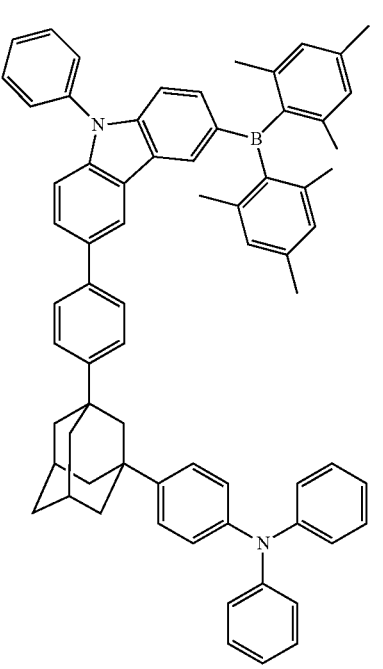
94

95
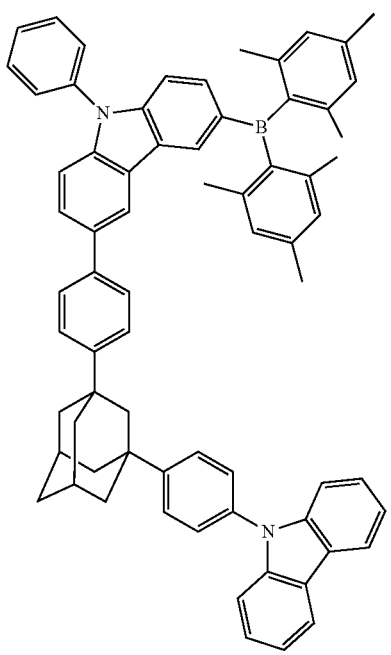
96
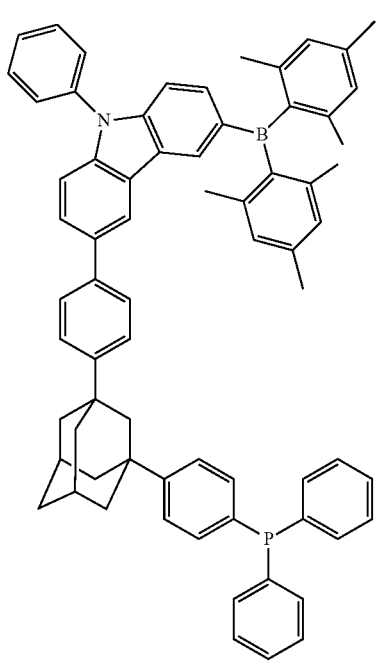
97
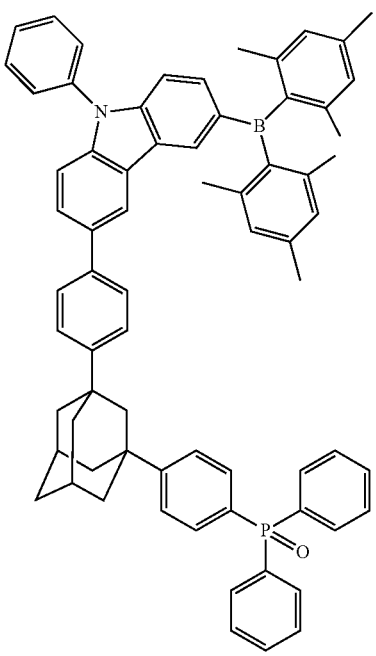
98
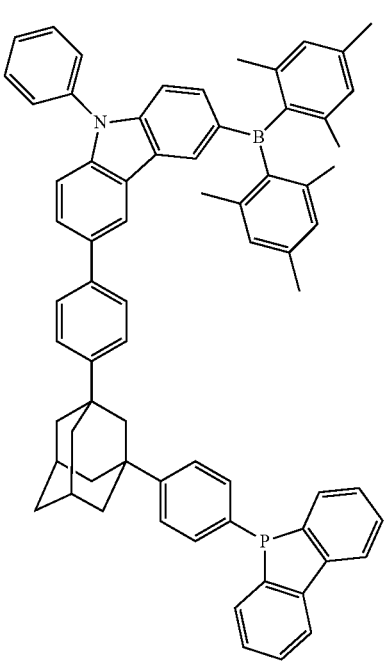

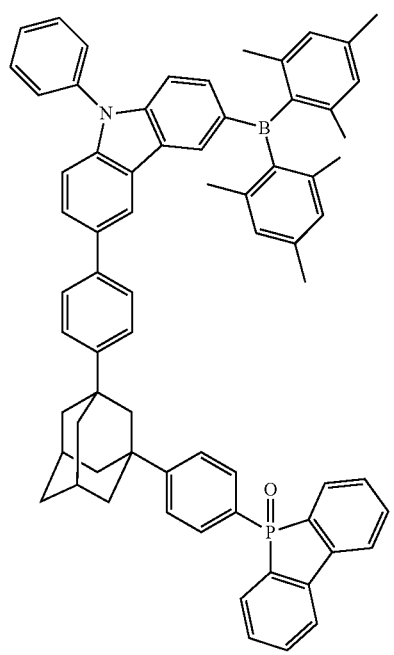
99
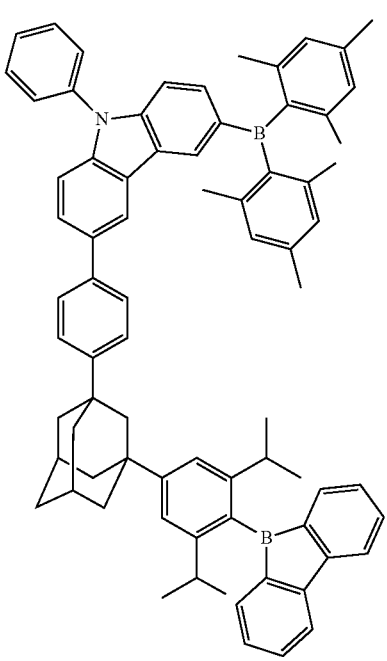
101
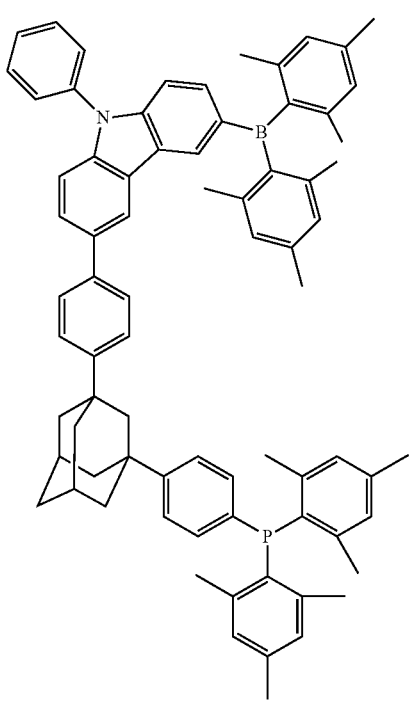
100
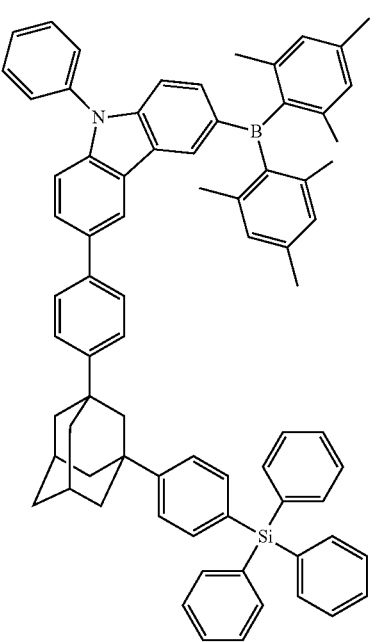
102

-continued
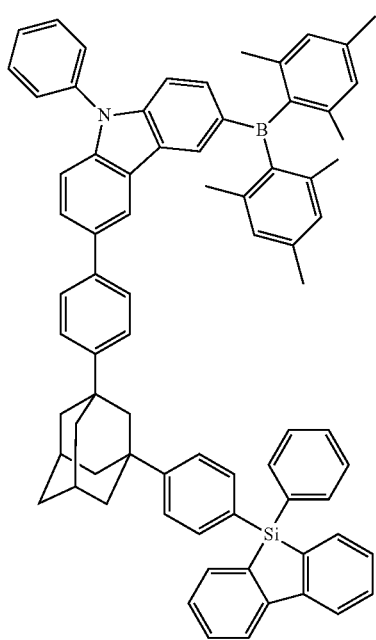
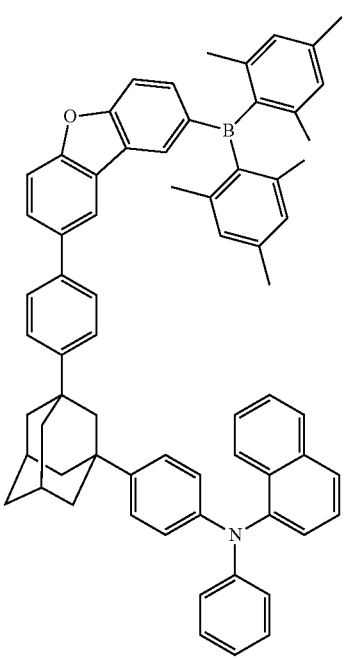

107
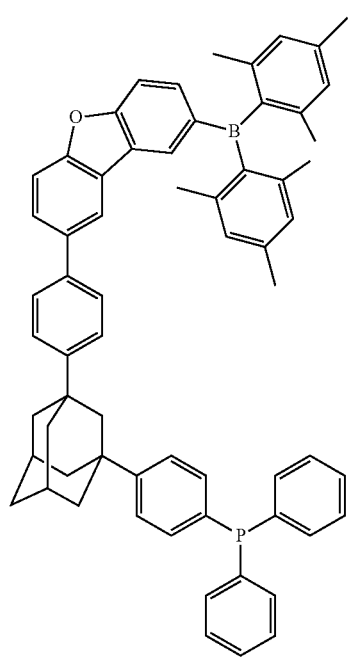
108
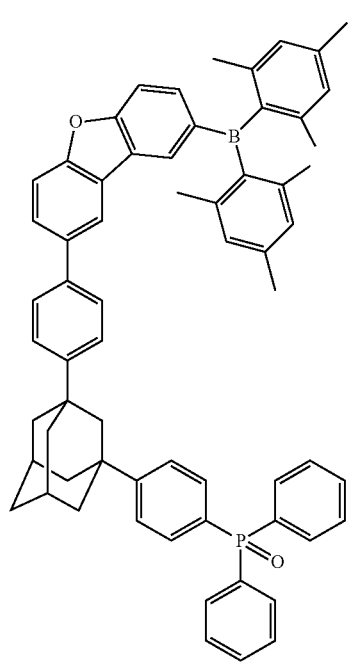
109
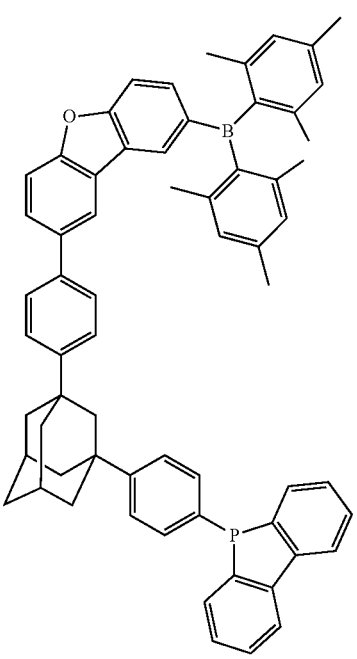
110
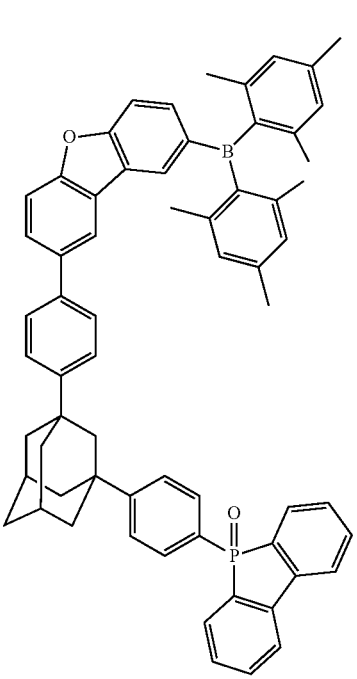

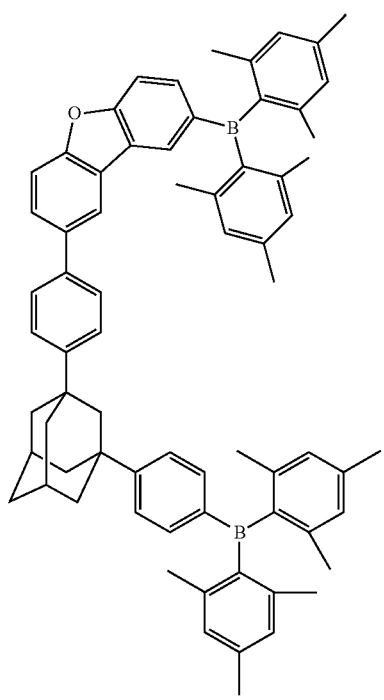
111
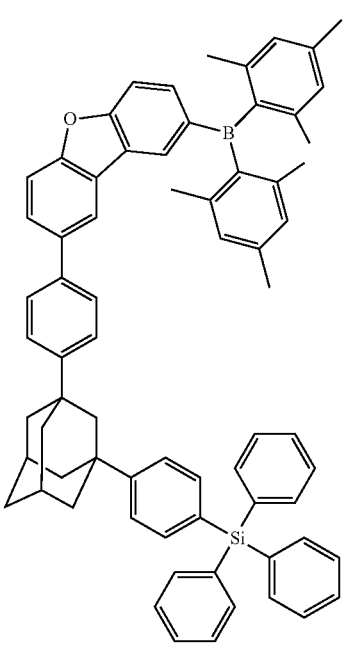
113
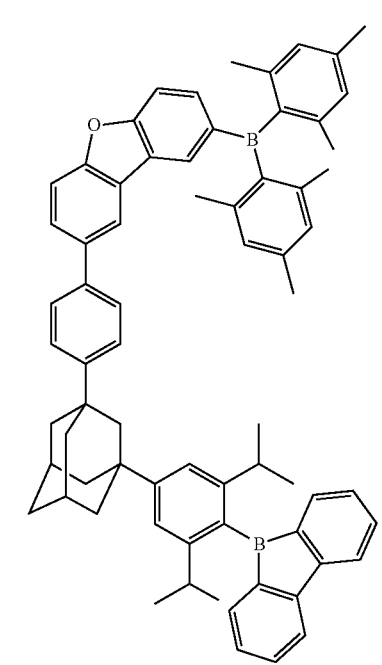
112
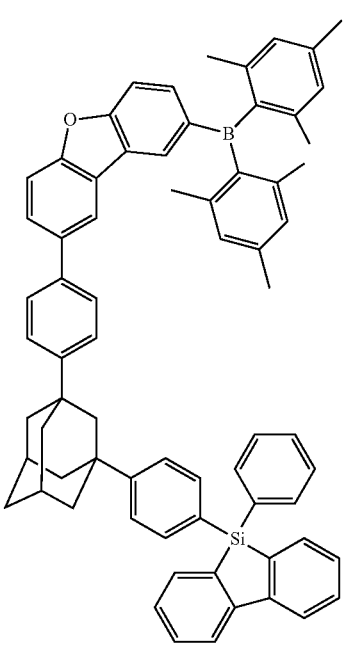
114

115 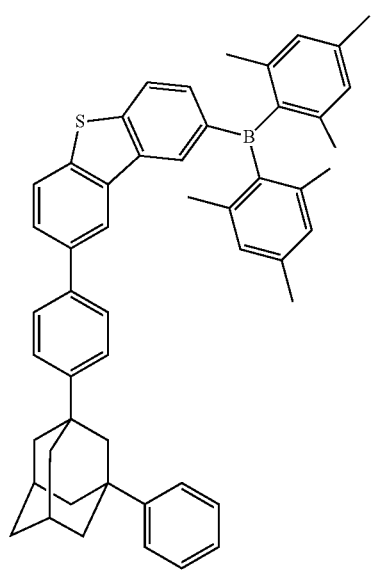
117 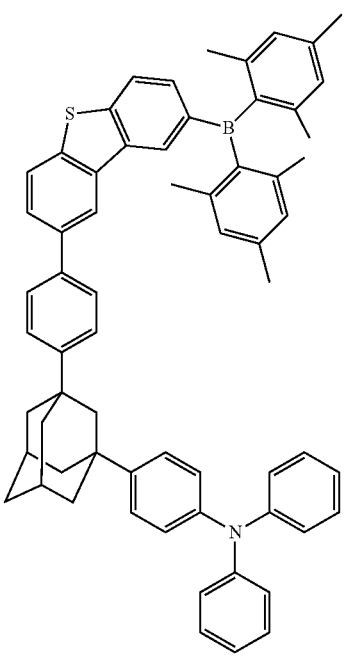
116 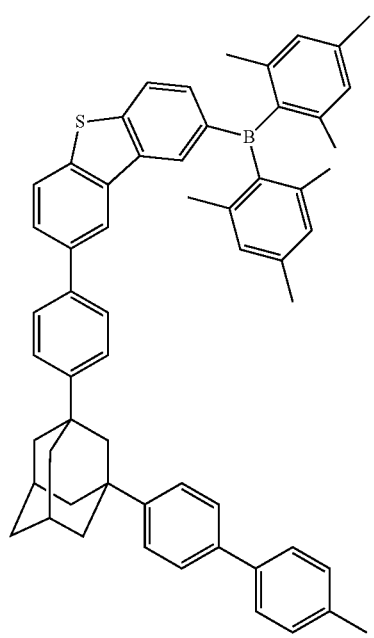
118 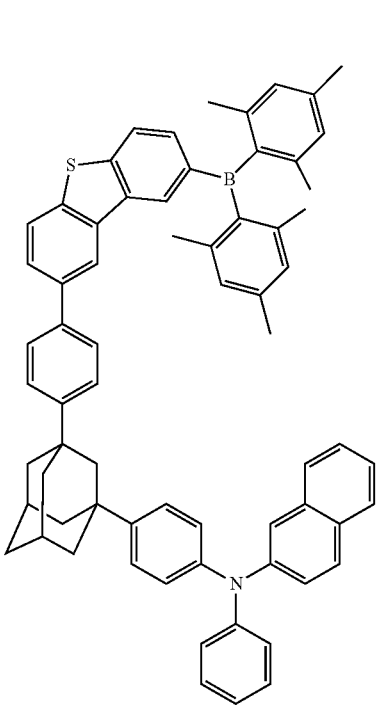

119
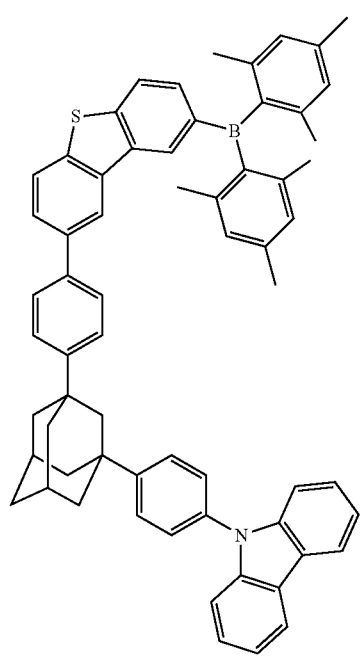
120
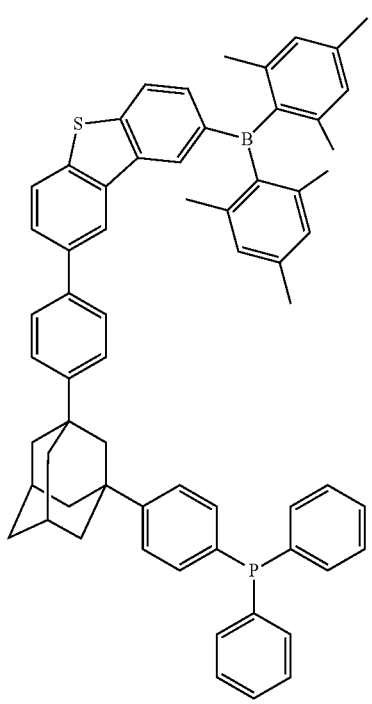
121
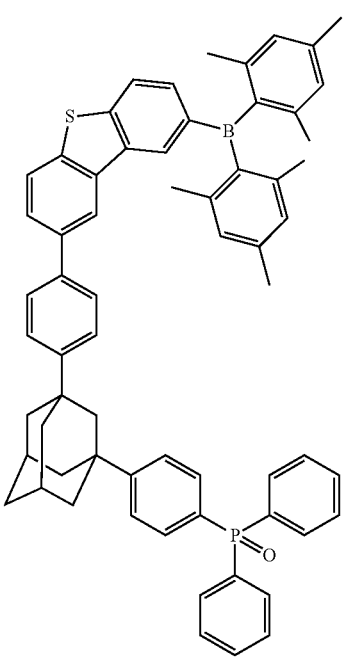
122
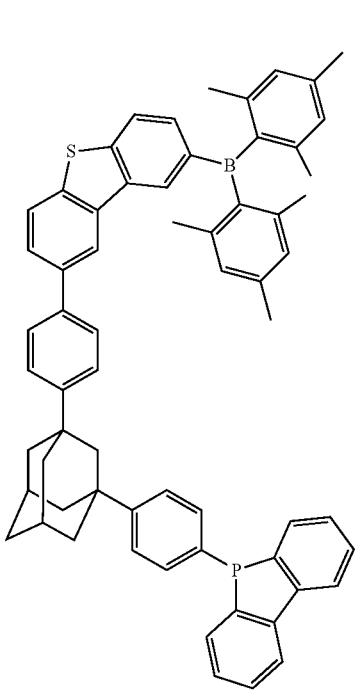

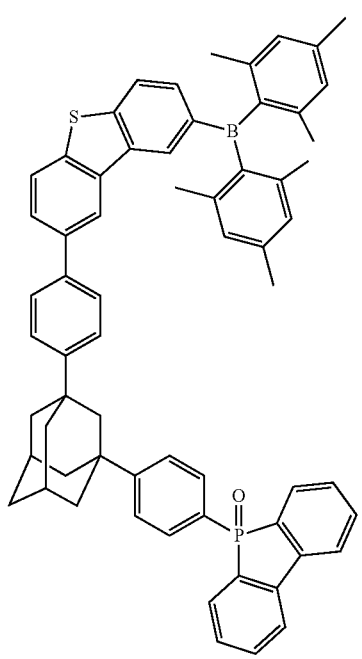
123
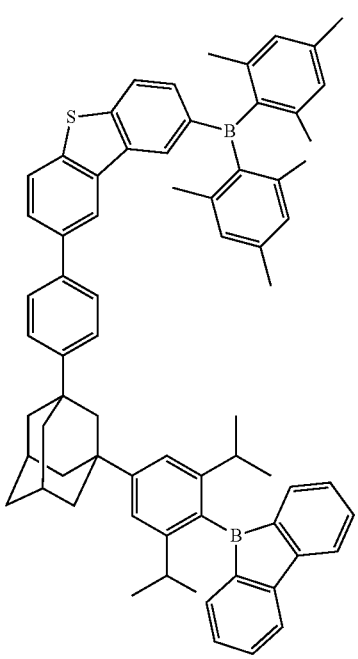
125
124
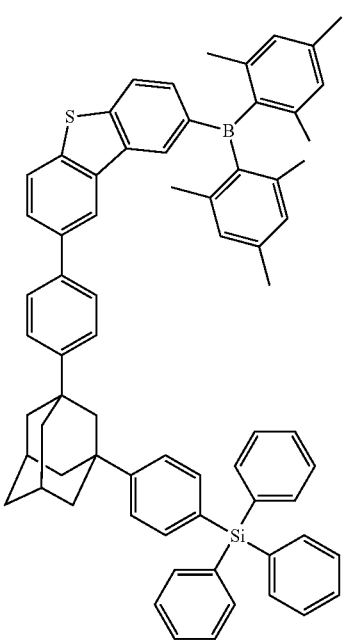
126

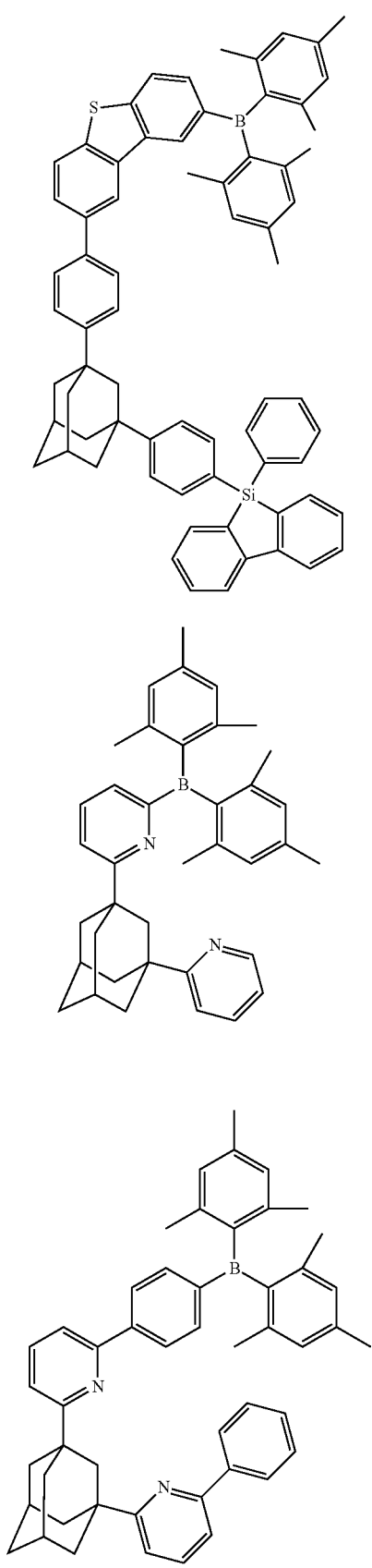
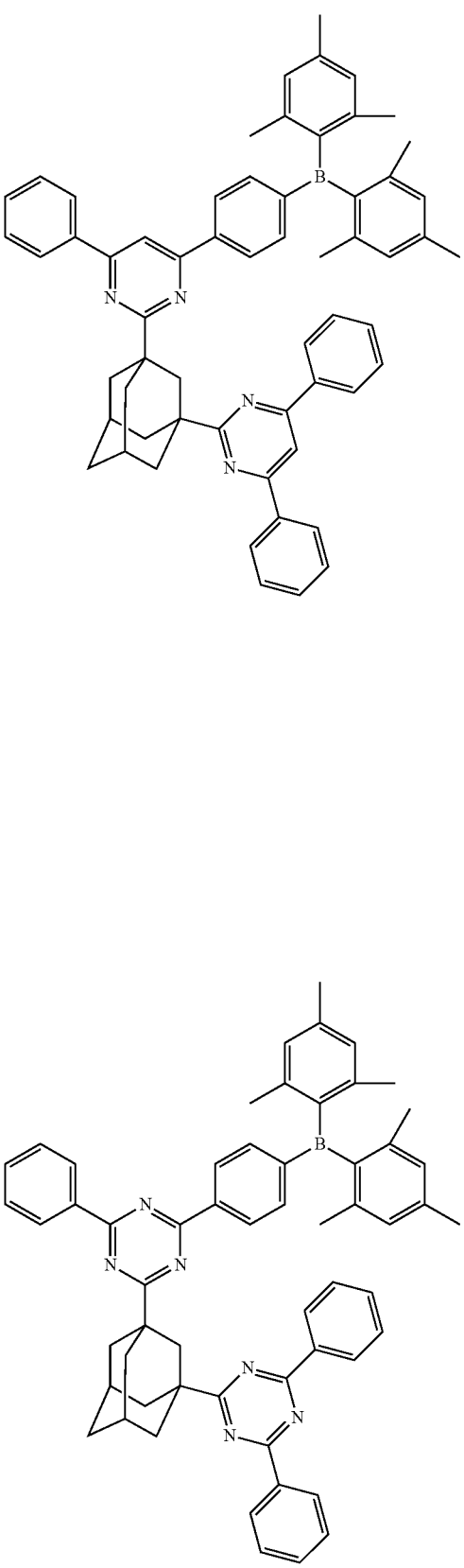

132
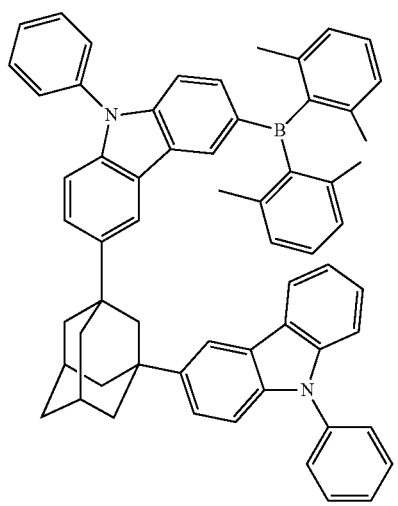
133
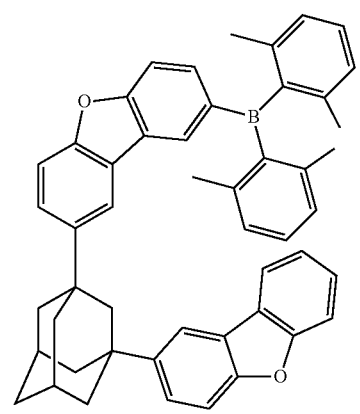
134
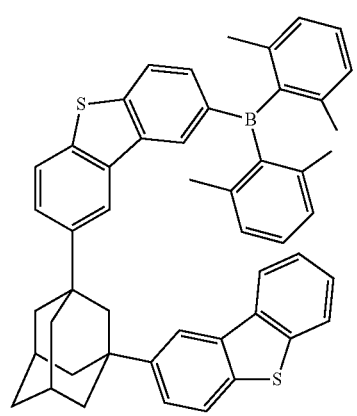
135
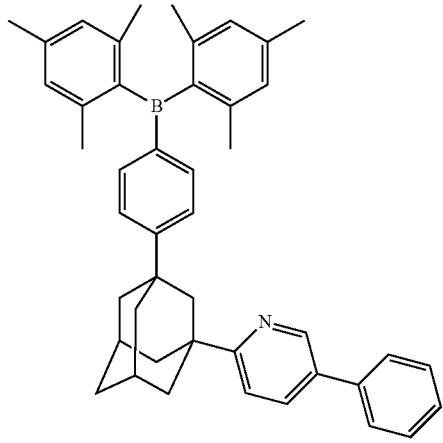
136
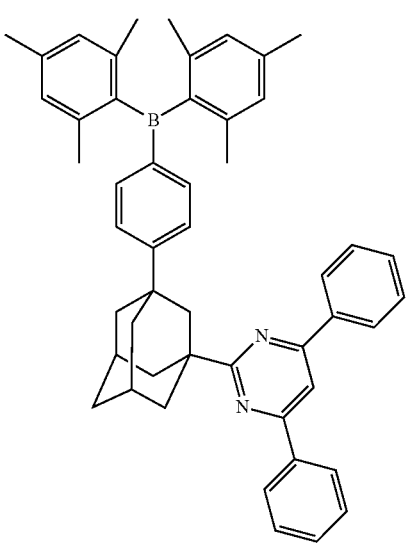
137
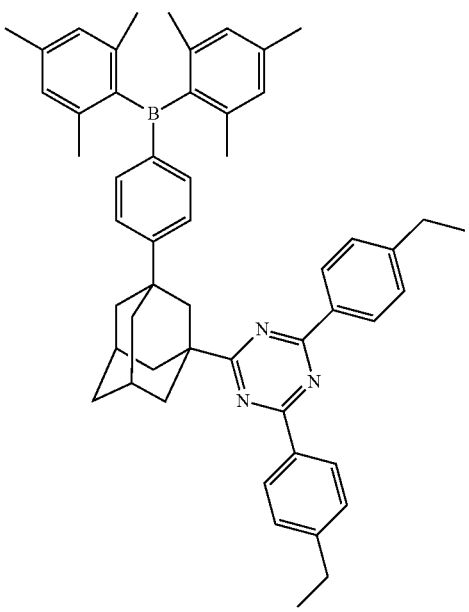

75
-continued
138
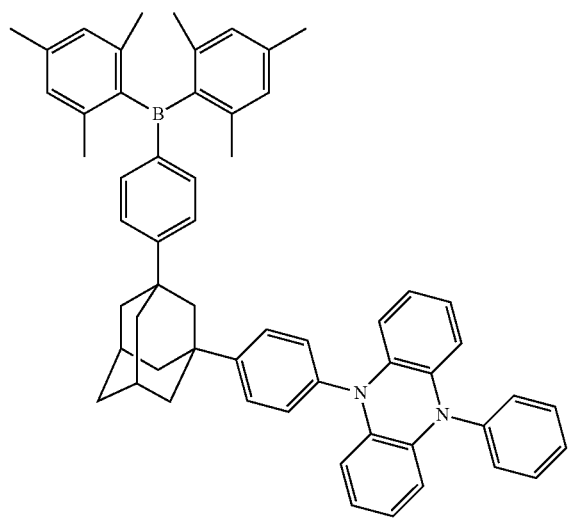
139
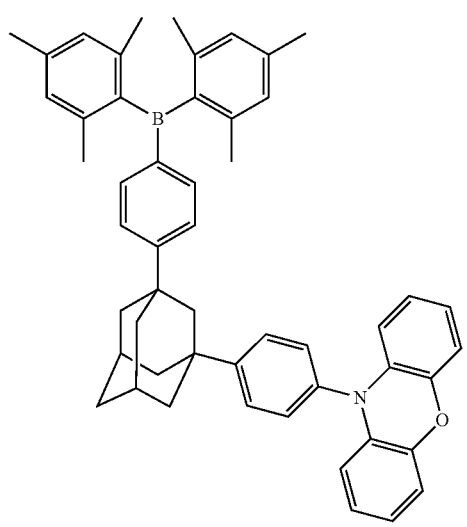
140
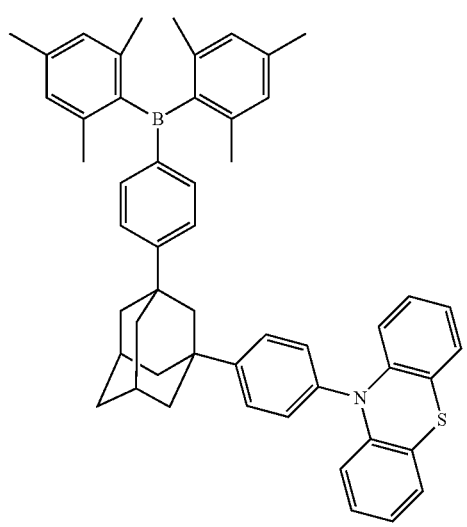
76
-continued
141
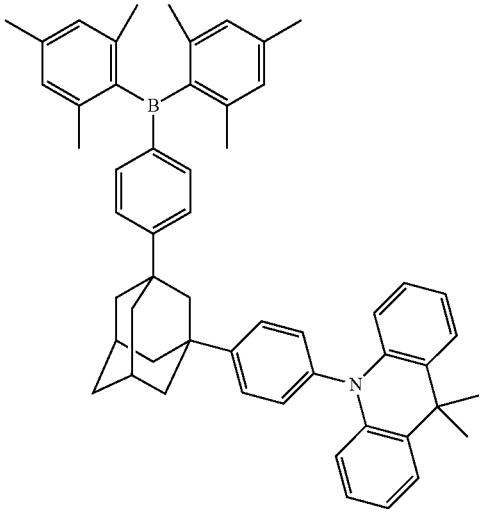
142
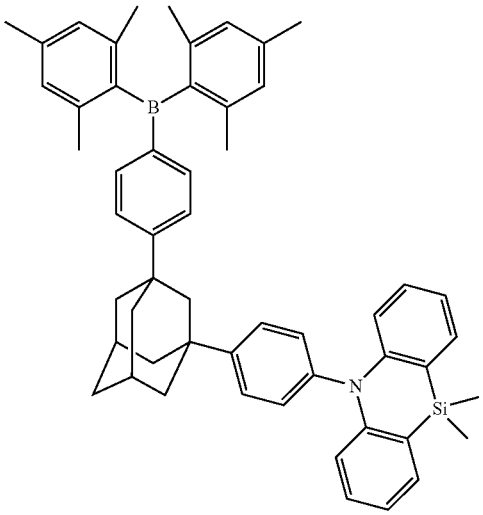
143
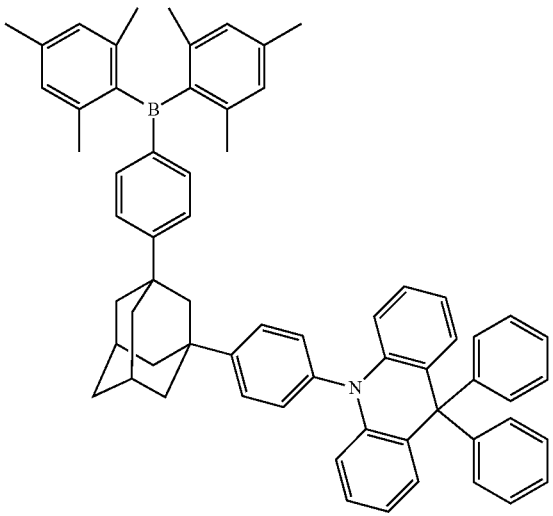

144

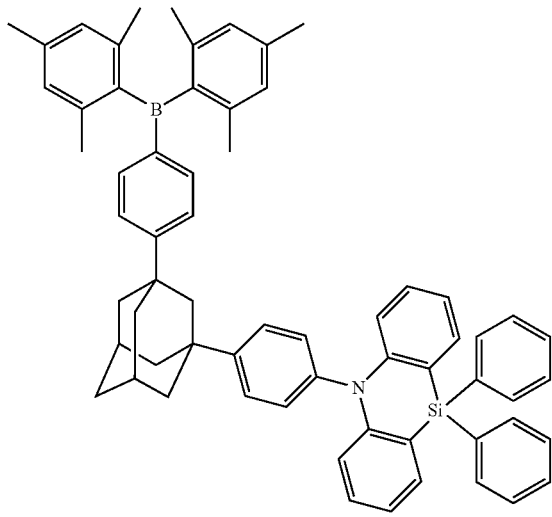

When the compound for an organic EL device represented by any one of the general formulae (1) to (3) (hereinafter sometimes referred to as compound of the present invention) is contained in at least one of a plurality of organic layers of an organic EL device formed by laminating an anode, the plurality of organic layers, and a cathode on a substrate, an excellent organic EL device is provided. A light-emitting layer, a hole-transporting layer, an electron-transporting layer, a hole-blocking layer, or an electron-blocking layer is suitable as the organic layer in which the compound is contained. Herein, when the compound of the present invention is used in the light-emitting layer, the compound can be used as a host material for the light-emitting layer containing a dopant. In addition, the compound of the present invention can be used as an organic light-emitting material that radiates fluorescence and delayed fluorescence, Herein, as the host material, there are given a phosphorescent host material, a fluorescent host material, and a delayed fluorescent host material. In the case where the compound of the present invention is used as the organic light-emitting material that radiates fluorescence and delayed fluorescence, it is preferred to use as the host material an organic compound in which at least one value of singlet excitation energy or triplet excitation energy is higher than that of the organic light-emitting material. In addition, the compound of the present invention is particularly preferably contained as a host material for the light-emitting layer containing a phosphorescent light-emitting dopant.

Next, an organic EL device of the present invention is described.

The organic EL device of the present invention includes organic layers including at least one light-emitting layer between an anode and a cathode laminated on a substrate. In addition, at least one of the organic layers contains the compound of the present invention. The compound of the present invention is advantageously contained in the light-emitting layer together with a phosphorescent light-emitting dopant.

Next, the structure of the organic EL device of the present invention is described with reference to the drawings. However, the structure of the organic EL device of the present invention is not limited to one illustrated in the drawings.

FIG. 1 is a sectional view for illustrating a structure example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may include an exciton-blocking layer adjacent to the light-emitting layer, or may include an electron-blocking layer between the light-emitting layer and the hole-injecting layer. The excitors-blocking layer may be inserted on any of the cathode side and the cathode side of the light-emitting layer, and may also be inserted simultaneously on both sides. The organic EL device of the present invention includes the substrate, the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It is possible to adopt a reverse structure as compared to FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated if necessary.

—Substrate—

The organic EL device of the present invention is preferably supported by a substrate. The substrate is not particularly limited, and any substrate that has been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals, such as Au, and conductive transparent materials, such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by using a method such as vapor deposition or sputtering and form a pattern having a desired shape thereon by photolithography. Alternatively, in the case of not requiring high pattern accuracy (about 100 µm or more), a pattern may be formed via a mask having a desired shape when any of the above-mentioned electrode substances is subjected to vapor deposition or sputtering. Alternatively, when a coatable substance, such as an organic conductive compound, is used, it is also possible to use a wet film-forming method, such as a printing method or a coating method. When luminescence is taken out from the anode, the transmittance of the anode is desirably controlled to more than 10%. Further, the sheet resistance as the anode is preferably several hundred Ω/□ or less. Further, the thickness of the film is, depending on its material, selected from usually the range of from 10 nm to 1,000 nm, preferably the range of from 10 nm to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than that of the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of an electron-injecting property and durability against oxidation or the like. The cathode may be produced by forming any of those electrode substances into a thin film by using a method such as vapor deposition or sputtering. Further, the sheet resistance as the cathode is preferably several hundred Ω/□ or less, and the thickness of the film is selected from usually the range of from 10 nm to 5 μm, preferably the range of from 50 nm to 200 nm. It should be noted that any one of the anode and cathode of the organic EL device is preferably transparent or semi-transparent because emitted light is transmitted therethrough and the light emission luminance improves.

Further, after any of the above-mentioned metals is formed into a film having a thickness of from 1 nm to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer is a layer that emits light after the production of an exciton by the recombination of a hole injected from the anode and an electron injected from the cathode, and the light-emitting layer contains an organic light-emitting material and a host material.

When the light-emitting layer is a fluorescent light-emitting layer, a fluorescent light-emitting material may be used alone in the light-emitting layer. However, it is preferred that the fluorescent light-emitting material be used as a fluorescent light-emitting dopant and the host material be mixed.

The compound of the present invention may be used as the fluorescent light-emitting material in the light-emitting layer. However, the fluorescent light-emitting material is known through, for example, many patent literatures, and hence may be selected from such known materials. Examples thereof include a benzoxazole derivative, a benzothiazole derivative, a benzimidazole derivative, a styrylbenzene derivative, a polyphenyl derivative, a diphenylbutadiene derivative, a tetraphenylbutadiene derivative, a naphthalimide derivative, a coumarine derivative, a fused aromatic compound, a perinone derivative, an oxadiazole derivative, an oxazine derivative, an aldazine derivative, a pyrrolidine derivative, a cyclopentadiene derivative, a bisstyrylanthracene derivative, a quinacridone derivative, a pyrrolopyridine derivative, a thiadiazolopyridine derivative, a styrylamine derivative, a diketopyrrolopyrrole derivative, an aromatic dimethylidene compound, various metal complexes typified by a metal complex of an 8-quinolinol derivative, and a metal complex, rare earth complex, or transition metal complex of a pyrromethene derivative, polymer compounds, such as polythiophene, polyphenylene, and polyphenylene vinylene, and an organic silane derivative. Of those, for example, the following compound is preferred: a fused aromatic derivative, a styryl derivative, a diketopyrrolopyrrole derivative, an oxazine derivative, or a pyrromethene metal complex, transition metal complex, or lanthanoid complex. For example, the following compound is more preferred: naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, naphtho[2,1-f]isoquinoline, α-naphthaphenanthridine, phenanthroxazole, quinolino[6,5-f]quinoline, or benzothiophanthrene. Those compounds may each have an alkyl group, aryl group, aromatic heterocyclic group, or diarylamino group as a substituent.

The compound of the present invention represented by any one of the general formulae (1) to (3) may be used as a fluorescent host material in the light-emitting layer. However, the fluorescent host material is known through, for example, many non patent literatures and patent literatures, and hence may be selected from such known materials. For example, the following material may be used: a compound having a fused aryl ring, such as naphthalene, anthracene, phenanthrene, pyrene, chrysene, naphthalene, triphenylene, perylene, fluoranthene, fluorene, or indene, or a derivative thereof; an aromatic amine derivative, such as N,N'-dinaphthyl-N,N'-diphenyl-4,4'-diphenyl-1,1'-diamine; a metal chelated oxinoid derivative, such as tris(8-quinolinato)aluminum(III); a bisstyryl derivative, such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative, such as a polyphenylene vinylene derivative, a poly-p-phenylene derivative, a polyfluorene derivative, a polyvinyl carbazole derivative, or a polythiophene derivative. However, the fluorescent host material is not particularly limited thereto.

When the fluorescent light-emitting material is used as a fluorescent light-emitting dopant and the host material is contained, the content of the fluorescent light-emitting dopant in the light-emitting layer desirably falls within the range of from 0.01 wt % to 20 wt %, preferably from 0.1 wt % to 10 wt %.

An organic EL device typically injects charges from both of its electrodes, i.e., its anode and cathode into a light-emitting substance to produce a light-emitting substance in an excited state, and causes the substance to emit light. In the case of a charge injection-type organic EL device, 25% of the produced excitons are said to be excited to a singlet excited state and the remaining 75% are said to be excited to a triplet excited state. As described in Advanced Materials 2009, 21, 4802, it has been known that after a specific fluorescent light-emitting substance has undergone an energy transition to a triplet excited state as a result of intersystem crossing or the like, the substance is subjected to inverse intersystem crossing to a singlet excited state by triplet-triplet annihilation or the absorption of thermal energy to radiate fluorescence, thereby expressing thermally activated delayed fluorescence. The organic EL device using the compound of the present invention can also express delayed fluorescence. In this case, the light emission may include both fluorescent light emission and delayed fluorescent light emission.

When the light-emitting layer is a delayed fluorescent light-emitting layer, a delayed fluorescent light-emitting material may be used alone in the light-emitting layer. However, it is preferred that the delayed fluorescent light-emitting material be used as a delayed fluorescent light-emitting dopant and the host material be mixed.

Although the compound of the present invention represented by any one of the general formulae (1) to (3) may be used as the delayed fluorescent light-emitting material in the light-emitting layer, a material selected from known delayed fluorescent light-emitting materials may also be used. There are given, for example, an indolocarbazole derivative disclosed in Appl. Phys. Lett. 98, 083302 (2011), a carbazole derivative disclosed in Nature 492, 234 (2012), and the like, but the delayed fluorescent light-emitting material is not limited to these compounds.

Specific examples of the delayed fluorescent light-emitting material are shown below, but the delayed fluorescent light-emitting material is not limited to the following compounds.

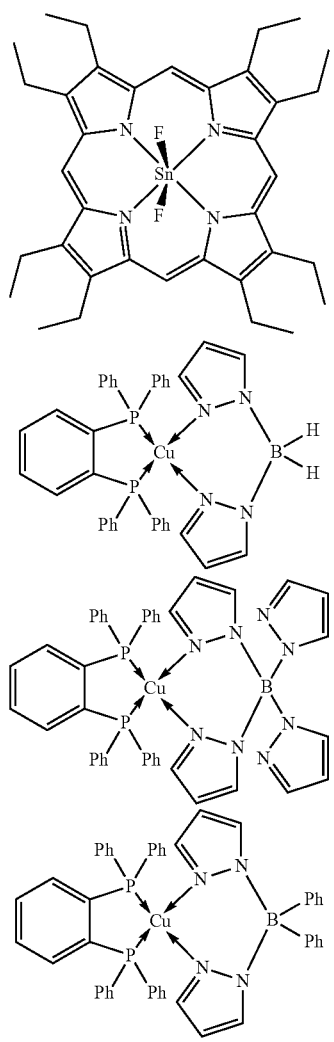

-continued

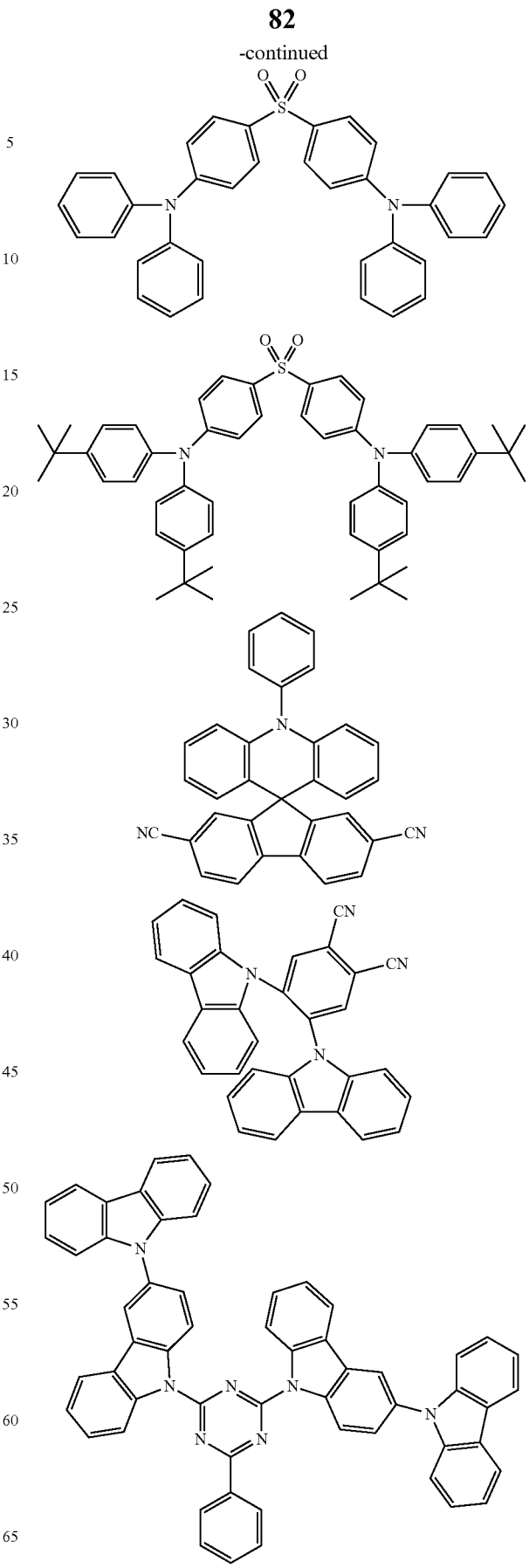

-continued

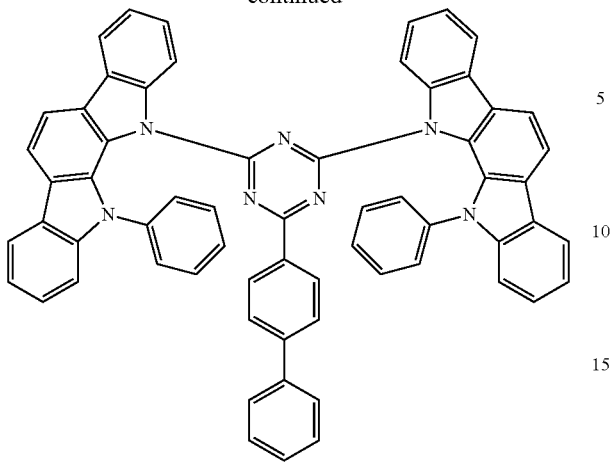

When the delayed fluorescent light-emitting material is used as a delayed fluorescent light-emitting dopant and the host material is contained, the content of the delayed fluorescent light-emitting dopant in the light-emitting layer desirably falls within the range of from 0.01 wt % to 50 wt %, preferably from 0.1 wt % to 20 wt %, more preferably from 0.01% to 10%.

The compound of the present invention represented by anyone of the general formulae (1) to (3) may be used as the fluorescent light-emitting material in the light-emitting layer. However, the delayed fluorescent host material may be selected from compounds other than the adamantane compound. For example, the following compound may be used: a compound having a fused aryl ring, such as naphthalene, anthracene, phenanthrene, pyrene, chrysene, naphthacene, triphenylene, perylene, fluoranthene, fluorene, or indene, or a derivative thereof; an aromatic amine derivative, such as N,N'-dinaphthyl-N,N'-diphenyl-4,4'-diphenyl-1,1'-diamine; a metal chelated oxinoid compound typified by tris(8-quinolinato)aluminum(III); a bisstyryl derivative, such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative, such as a polyphenylene vinylene derivative, a poly-p-phenylene derivative, a polyfluorene derivative, a polyvinyl carbazole derivative, a polythiophene derivative, or an arylsilane derivative. However, the delayed fluorescent host material is not particularly limited thereto.

In the case where the light-emitting layer is a phosphorescent light-emitting layer, the light-emitting layer contains a phosphorescent light-emitting dopant and a host material. The phosphorescent light-emitting dopant material is known through many literatures, and may be selected from such known materials. There are given, for example, an iridium complex disclosed in J. Am. Chem, Soc. 2001, 123, 4303, a platinum complex disclosed in Nature 395, 151 (1997), and the like, but the phosphorescent light-emitting dopant material is not limited to these compounds.

Preferred examples of the phosphorescent light-emitting dopant include complexes such as Ir(ppy)3, complexes such as Ir(bt)2.acac3, and complexes such as PtOEt3, the complexes each having a noble metal element, such as Ir, as a central metal. Specific examples of those complexes are shown below, but the complexes are not limited to the compounds described below.

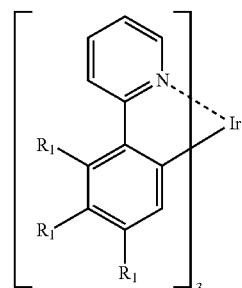

$R_1$: H, $CH_3$, $CF_3$, F

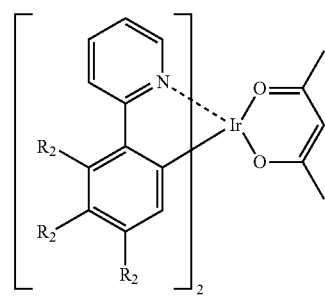

$R_2$: H, F

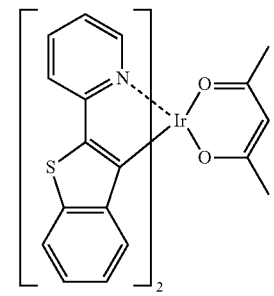

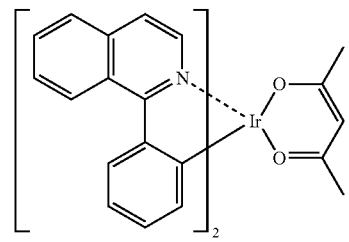

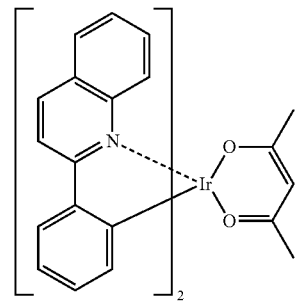

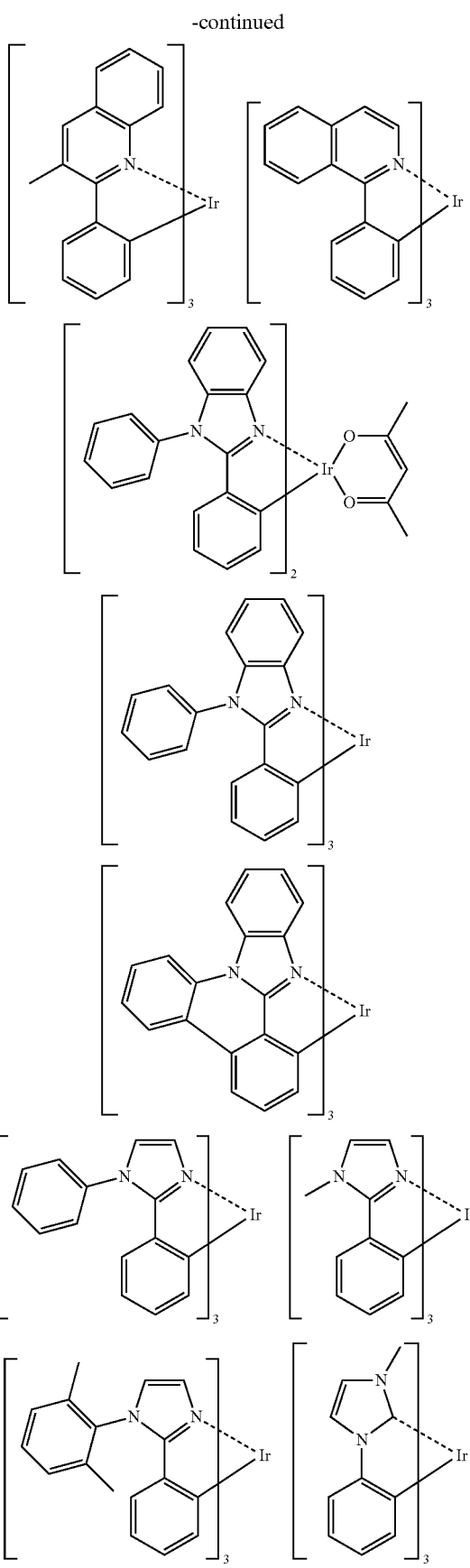
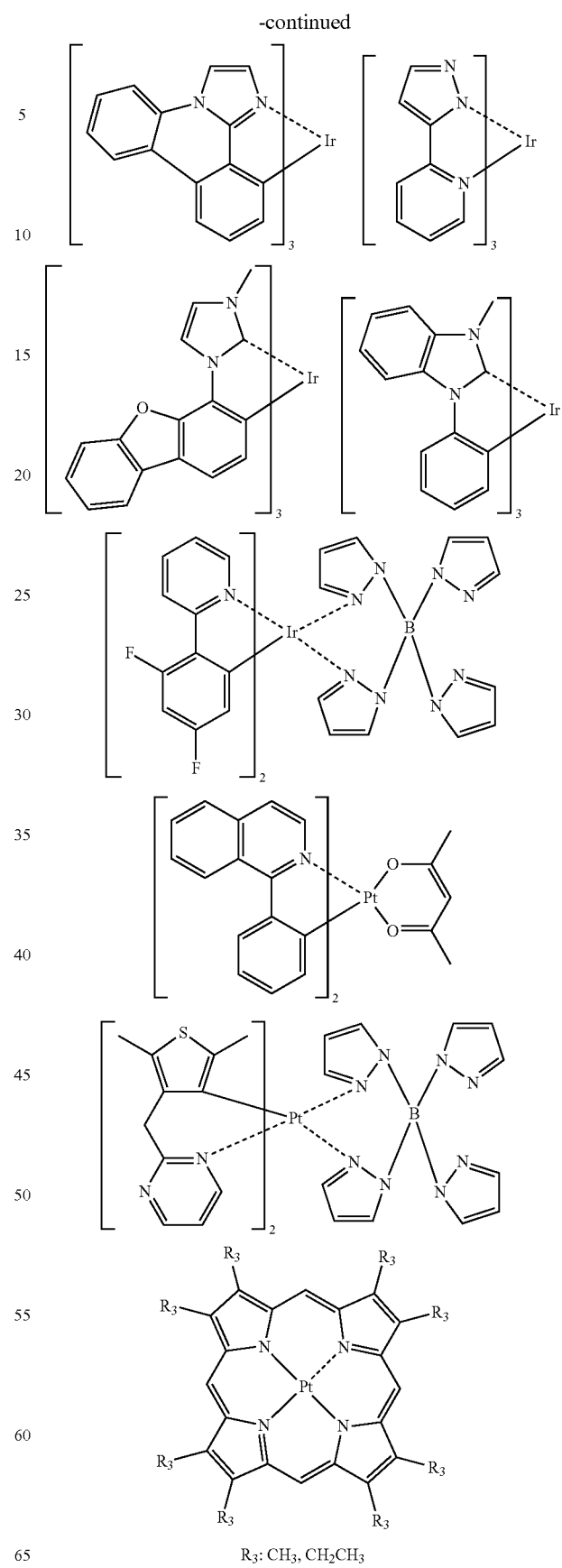

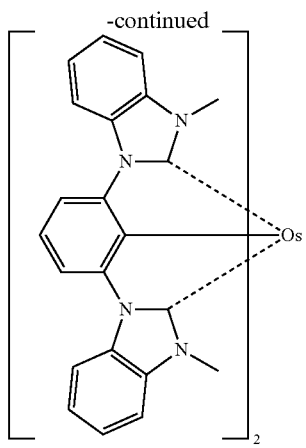

It is desired that the content of the phosphorescent light-emitting dopant in the light-emitting layer be in the range of from 2 wt % to 40 wt %, preferably from 5 wt % to 30 wt. %.

When the light-emitting layer is a phosphorescent light-emitting layer, it is preferred to use, as a host material in the light-emitting layer, the compound of the present invention represented by any one of the general formulae (1) to (3). However, when the compound of the present invention is used in any of the organic layers other than the light-emitting layer, the material to be used in the light-emitting layer may be another host material other than the adamantane compound, or the compound of the present invention and any other host material may be used in combination. Further, a plurality of kinds of known host materials may be used in combination.

It is preferred to use, as a known host compound that may be used, a compound that has a hole-transporting ability or an electron-transporting ability, is capable of preventing luminescence from having a longer wavelength, and has a high glass transition temperature.

Such other host materials are known through, for example, many patent literatures, and hence may be selected from such known materials. Specific examples of the host material include, but are not particularly limited to, an indole derivative, a carbazole derivative, an indolocarbazole derivative, a triazole derivative, an oxazole derivative, an oxadiazole derivative, an imidazole derivative, a polyarylalkane derivative, a pyrazoline derivative, apyrazolone derivative, aphenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride, such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds, such as a polysilane-based compound, a poly (N-vinylcarbazole) derivative, an aniline-based copolymer, a thiophene oligomer, a polythiophene derivative, a polyphenylene derivative, a polyphenylenevinylene derivative, and a polyfluorene derivative.

The light-emitting layer, which may be any one of a fluorescent light-emitting layer, a delayed fluorescent light-emitting layer, and a phosphorescent light-emitting layer, is preferably the phosphorescent light-emitting layer.

—Injecting Layer—

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole in the light-emitting layer by blocking holes while transporting electrons.

It is preferred to use the compound of the present invention represented by any one of the general formulae (1) to (3) for the hole-blocking layer. However, when the compound of the present invention is used in any other organic layer, a known material for a hole-blocking layer may be used. Further, as a material for the hole-blocking layer, a material for the electron-transporting layer to be described later may be used as required.

—Electron-Blocking Layer—

The electron-blocking layer has, in a broad sense, the function of an hole-transporting layer, and is capable of improving the probability of recombining an electron and a hole in the light-emitting layer by blocking electrons while transporting holes.

The compound of the present invention represented by any one of the general formulae (1) to (3) according to the present invention may be used as a material for the electron-blocking layer. However, another material, i.e., a material for the hole-transporting layer to be described later may be used as required. The thickness of the electron-blocking layer is preferably from 3 nm to 100 nm, more preferably from 5 nm to 30 nm.

—Exciton-Blocking Layer—

The exciton-blocking layer refers to a layer for blocking excitons produced by the recombination of a hole and an electron in the light-emitting layer from diffusing into charge-transporting layers. Inserting this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

The compound of the present invention represented by any one of the general formulae (1) to (3) may be used as a material for the exciton-blocking layer. However, as other materials therefor, there are given, for example, 1,3-dicarbazolylbenzene (mCP) and bis(2-methyl-8-quinolinolato)-4-phenylphenolatoaluminum (III) (BAlq).

—Hole-Transporting Layer—

The hole-transporting layer is formed of a hole-transporting material having a function of transporting holes, and a single hole-transporting layer or a plurality of hole-transporting layers may be formed.

The hole-transporting material has a hole-injecting property or a hole-transporting property or has an electron-blocking property, and any of an organic material and an inorganic material may be used as the hole-transporting material. It is preferred to use the adamantane compound represented by any one of the general formulae (1) to (3) for the hole-transporting layer. However, any compound selected from conventionally known compounds may be used. Examples of the known hole-transporting material that may be used include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be formed.

An electron-transporting material (which also serves as a hole-blocking material in some cases) only needs to have a function of transferring electrons injected from the cathode into the light-emitting layer. It is preferred to use the compound of the present invention represented by any one of the general formulae (1) to (3) according to the present invention for the electron-transporting layer. However, any compound selected from conventionally known compounds may be used. Examples thereof include a nitro-substituted fluorene derivative, a diphenylquinone derivative, a thiopyran dioxide derivative, a carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative that has a quinoxaline ring known as an electron withdrawing group. Further, it is also possible to use a polymer material in which any of those materials is introduced in a polymer chain or is used as a polymer main chain.

EXAMPLES

The present invention is hereinafter described in more detail byway of Examples. It should be appreciated that the present invention is not limited to Examples below and may be carried out in various forms as long as the various forms do not deviate from the gist of the present invention.

The route described below was used to synthesize an adamantane compound to be used as a material for a phosphorescent light-emitting device. It should be noted that the number of each compound corresponds to the number given to the exemplified compound.

Example 1

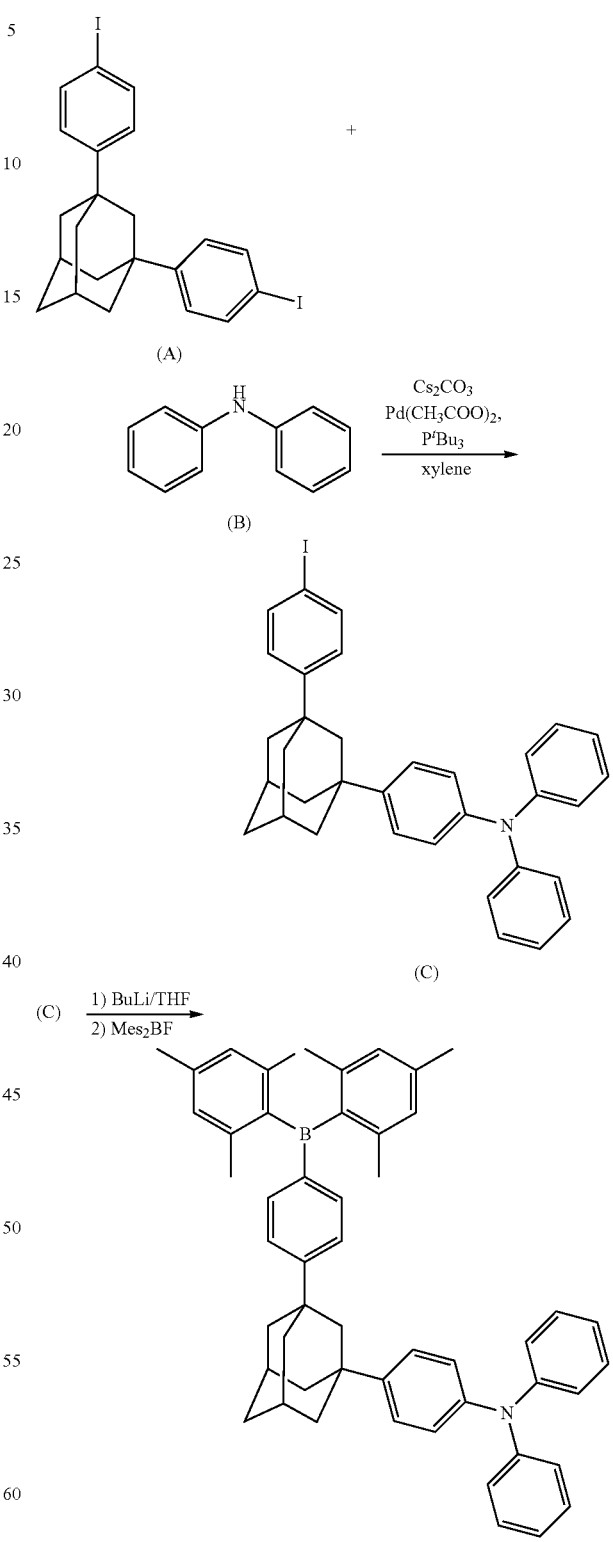

Under a nitrogen atmosphere, 5.00 g of a compound (A), 1.57 g of a compound (B), 27.14 g of cesium carbonate, 0.62 g of palladium acetate, and 150 ml of xylene were added and stirred at room temperature. Further, 1.12 g of tri-tert-butylphosphine was added thereto, followed by stirring at 150° C. for 1 hr. The reaction solution was cooled to room temperature, and then filtered. A residue obtained by concentrating the filtrate was purified by silica gel column chromatography to provide 1.72 g (yield: 36%) of an intermediate (C) as a white solid.

Under a nitrogen atmosphere, 1.72 g of the intermediate (C) and 50 ml of tetrahydrofuran were added and cooled to −78° C. 2 ml of butyllithium was added thereto, followed by stirring at −78° C. for 30 min. After that, 0.94 g of dimesitylfluoroborane was added thereto, followed by stirring at room temperature for 2 hr. The reaction solution was concentrated, and then the resultant residue was purified by silica gel column chromatography and recrystallization to provide 0.56 g (yield: 30%) of Compound 10 as a white solid.

Figure 2:
FIG. 2 is a 1H-NMR chart of Compound 10 for an organic EL device of the present invention.
Figure 3:
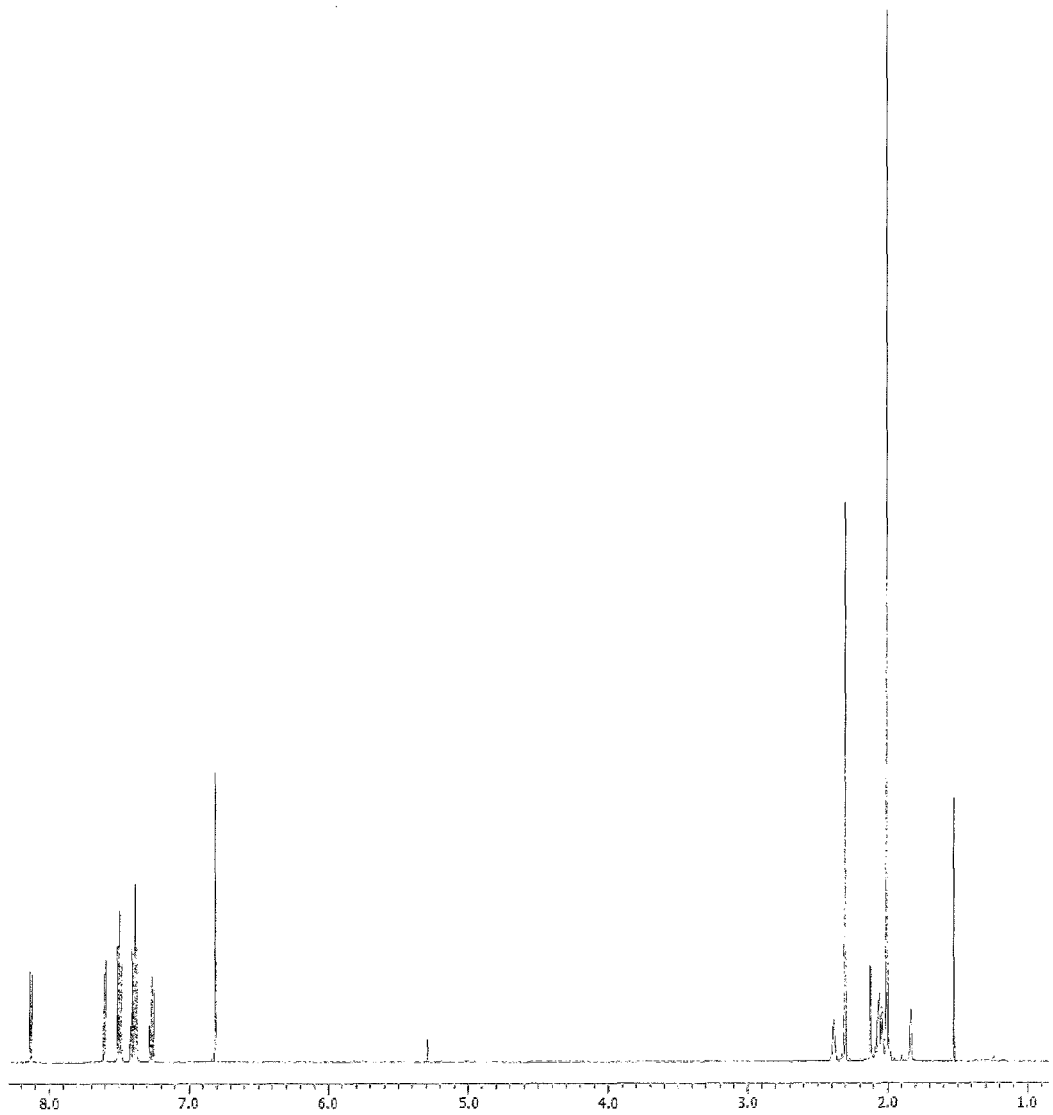
FIG. 3 is a 1H-NMR chart of Compound 15 for an organic EL device of the present invention.

The APCI-TOFMS of the compound showed an [M+1] peak at an m/z of 704. The results of its 1H-NMR measurement (measurement solvent: THF-d8) are shown in FIG. 2.

Example 2

Synthesis of Compound 15

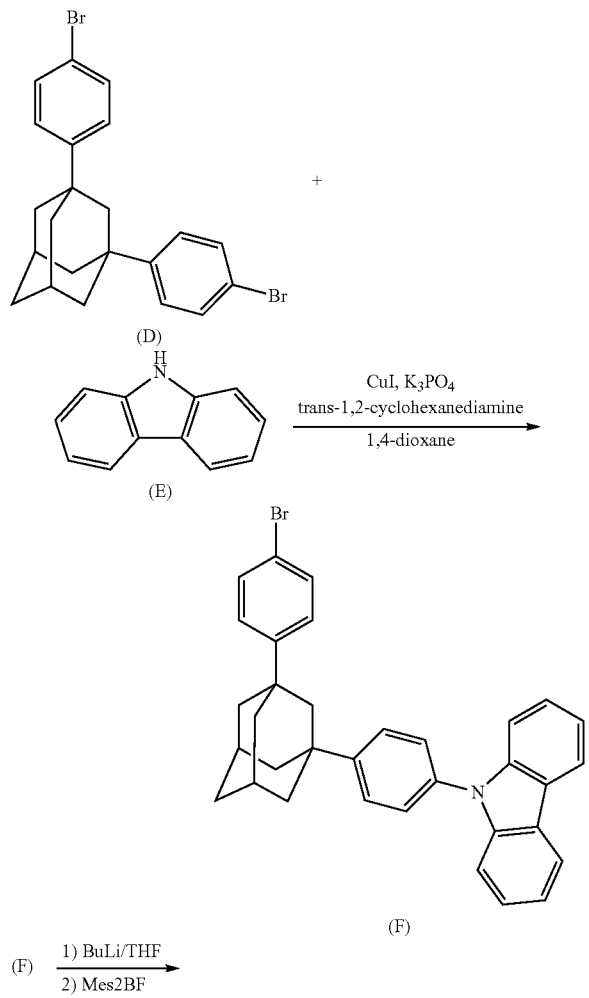

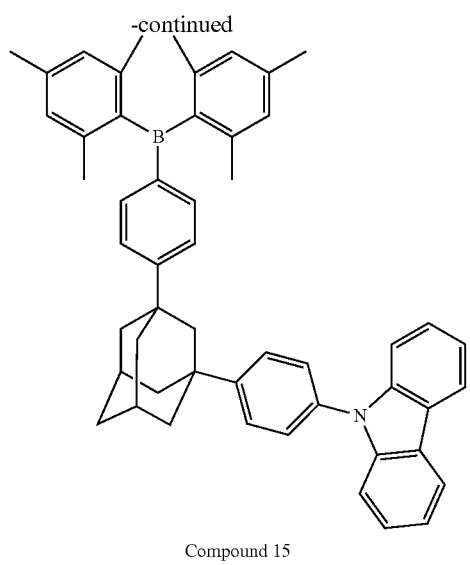

Compound 15

Under a nitrogen atmosphere, 8.73 g of a compound (D), 2.94 g of a compound (E), 19.02 g of tripotassium phosphate, 0.85 g of copper(I) iodide, and 500 ml of 1,4-dioxane were added and stirred at room temperature. Further, 5.11 g of trans-1,2-cyclohexanediamine was added thereto, followed by stirring at 110° C. for 8 hr. The reaction solution was cooled to room temperature, and then filtered. A residue obtained by concentrating the filtrate was purified by silica gel column chromatography to provide 4.03 g (yield: 39%) of an intermediate (F) as a white solid.

Under a nitrogen atmosphere, 4.03 g of the intermediate (F) and 100 ml of tetrahydrofuran were added and cooled to −60° C. 5.8 ml of butyllithium was added thereto, followed by stirring at −60° C. for 30 min. After that, 5.00 g of dimesitylfluoroborane was added thereto, followed by stirring at room temperature for 72 hr. The reaction solution was concentrated, and then the resultant residue was purified by silica gel column chromatography and recrystallization to provide 2.53 g (yield: 47%) of Compound 15 as a white solid.

The APCI-TOFMS of the compound showed an [M+1] peak at an m/z of 702. The results of its 1H-NMR measurement (measurement solvent: THF-d8) are shown in FIG. 2.

Example 3

Each thin film was laminated by a vacuum deposition method at a degree of vacuum of $4.0 \times 10^{-5}$ Pa on a glass substrate on which an anode formed of ITO having a thickness of 110 nm had been formed. First, copper phthalocyanine (CuPC) was formed into a layer having a thickness of 25 nm on the ITO. Next, 4,4'-bis[N-(1-naphthyl)-N-phenylamino]biphenyl (NPB) was formed into a layer having a thickness of 40 nm to serve as a hole-transporting layer. Next, Compound 10 as a host material and tris(2-phenylpyridine) iridium (III) (Ir (ppy)$_3$) as a phosphorescent light-emitting dopant were co-deposited from different deposition sources onto the hole-transporting layer to form a light-emitting layer having a thickness of 40 nm. The concentration of Ir(ppy)$_3$ in the light-emitting layer was 10.0 wt %. Next, Alq3 was formed into a layer having a thickness of 20 nm to serve as an electron-transporting layer. Further, lithium fluoride was formed into a layer having a thickness of 1.0 nm to serve as an electron-injecting layer on the electron-transporting layer. Finally, aluminum was formed into a layer having a thickness of 70 nm to serve as an electrode on the electron-injecting layer. Thus, an organic EL device was produced.

An external power source was connected to the resultant organic EL device to apply a DC voltage to the device. As a result, it was confirmed that the device had such light-emitting characteristics as shown in Table 1. The columns "luminance", "voltage", and "luminous efficiency" in Table 1 show values at 20 mA/cm². It was found that the local maximum wavelength of the emission spectrum of the device was 520 nm and hence light emission from Ir(ppy)$_3$ was obtained.

Examples 4 to 12

Compounds 2, 4, 16, 24, 37, 43, 72, and 91 were prepared in the same manner as in Examples 1 and 2.

Organic EL devices were each produced in the same manner as in Example 3 except that Compounds 2, 4, 15, 16, 24, 37, 43, 72, and 91 were each used instead of Compound 10 as the host material for the light-emitting layer. It was found that the local maximum wavelength of the emission spectrum of each of the devices was 520 nm, and hence light emission from Ir(ppy)$_3$ was obtained. The respective light-emitting characteristics are shown in Table 1.

Comparative Example 1

An organic EL device was produced in the same manner as in Example 3 except that CBP was used as the host for the light-emitting layer.

Comparative Examples 2 and 3

Organic EL devices were each produced in the same manner as in Example 3 except that the following compounds H-1 and H-2 were each used as the host for the light-emitting layer.

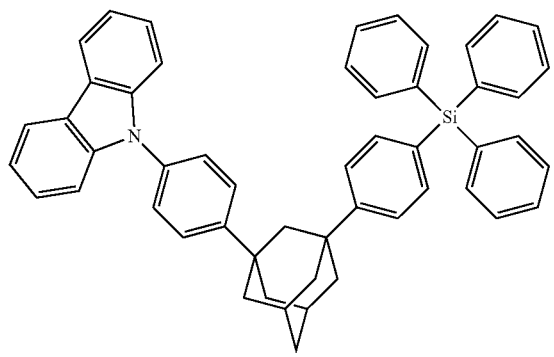

H-1

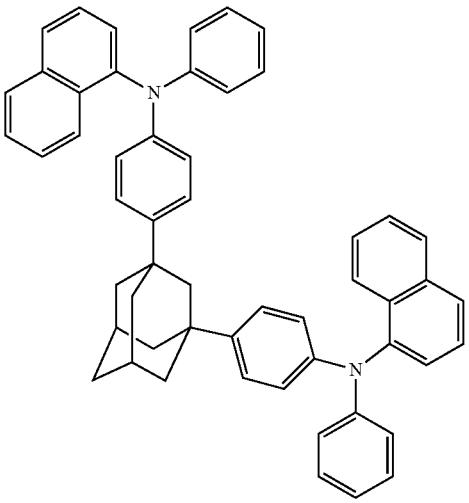

H-2

It was found that the local maximum spectrum of the emission spectrum of each of the organic EL devices produced in Comparative Examples 1 to 3 was 520 nm, and hence light emission from Ir(ppy)3 was obtained. The compounds each used as the host material and the respective light-emitting characteristics are shown in Table 1.

In Table 1, the values of the light-emitting characteristics are values at 20 mA/cm².

TABLE 1

| Example | Compound | Luminance (cd/m²) | Voltage (V) | Luminous efficiency (lm/W) |
|---|---|---|---|---|
| 3 | 10 | 5,300 | 5.0 | 16.6 |
| 4 | 2 | 5,050 | 5.5 | 14.4 |
| 5 | 4 | 4,930 | 4.9 | 15.8 |
| 6 | 15 | 5,470 | 5.5 | 15.6 |
| 7 | 16 | 5,140 | 5.2 | 15.5 |
| 8 | 24 | 5,080 | 5.0 | 16.0 |
| 9 | 37 | 5,330 | 5.6 | 14.9 |
| 10 | 43 | 5,010 | 4.9 | 16.1 |
| 11 | 72 | 4,970 | 5.4 | 14.4 |
| 12 | 91 | 5,630 | 5.5 | 16.1 |
| Comparative Example 1 | CBP | 4,700 | 9.5 | 7.8 |
| 2 | H-1 | 4,500 | 9.8 | 7.2 |
| 3 | H-2 | 4,330 | 8.6 | 7.9 |

It is found from Table 1 that the organic EL device using the adamantane compound represented by the general formula (1) has a low driving voltage and shows good luminous efficiency as compared to those in the case where CBP generally known as a phosphorescent host is used. It is also found that the device shows good luminous efficiency as compared to that in the case where H-1 or H-2 as the adamantane compound not having a triarylborane structure is used. The superiority of the organic EL device using the compound of the present invention is apparent from the foregoing.

INDUSTRIAL APPLICABILITY

The organic EL device according to the present invention has light-emitting characteristics, driving voltage, and durability at practically satisfactory levels. Thus, the organic EL device has a large technical value in applications to flat panel displays (display devices for mobile phones, in-vehicle display devices, display devices for OA computers, televisions, and the like), light sources utilizing characteristics of planar light emitters (light sources in lighting equipment and copying machines and backlight sources in liquid crystal displays and instruments), sign boards, sign lamps, and the like.

REFERENCE SIGNS LIST

1 substrate, 2 anode, 3 hole-injecting layer, 4 hole-transporting layer, 5 light-emitting layer, 6 electron-transporting layer, 7 cathode

The invention claimed is:
1. A compound for an organic electroluminescent device, which is represented by the following general formula (1):

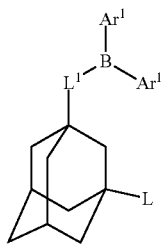

(1)

wherein,
L and $L^1$ each independently represent a monovalent or divalent group selected from a substituted or unsubstituted aromatic hydrocarbon group, a substituted or unsubstituted aromatic heterocyclic group, or a linked aromatic group formed by linking two to four of aromatic rings of the substituted or unsubstituted aromatic hydrocarbon groups and the substituted or unsubstituted aromatic heterocyclic groups, the linked aromatic group may be linear or branched, and the aromatic rings to be linked may be identical to or different from each other; and
$Ar^1$'s each independently represent a substituted or unsubstituted aromatic hydrocarbon group or a substituted or unsubstituted aromatic heterocyclic group.

2. A compound for an organic electroluminescent device according to claim wherein the compound is represented by the following general formula (2):

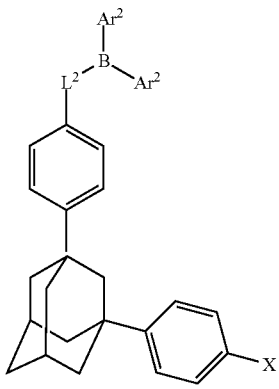

(2)

wherein,
$L^2$ represents a single bond or a divalent group selected from a substituted or unsubstituted aromatic hydrocarbon group, a substituted or unsubstituted aromatic heterocyclic group, or a linked aromatic group formed by linking two or three of aromatic rings of the substituted or unsubstituted aromatic hydrocarbon groups and the substituted or unsubstituted aromatic heterocyclic groups, the linked aromatic group may be linear or branched, and the aromatic rings to be linked may be identical to or different from each other;
$Ar^2$'s each independently represent a substituted or unsubstituted aromatic hydrocarbon group or a substituted or unsubstituted aromatic heterocyclic group; and
X represents hydrogen, a cyano group, an alkyl group, a diarylamino group, a triarylsilyl group, a diarylphosphinyl group, a diarylphosphine oxide group, a diarylboranyl group, a substituted or unsubstituted aromatic hydrocarbon group, or a substituted or unsubstituted aromatic heterocyclic group.

3. A compound for an organic electroluminescent device according to claim 2, wherein the compound is represented by the following general formula (3):

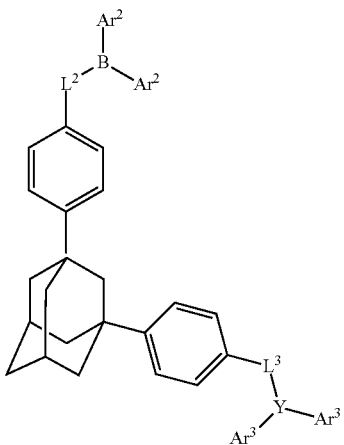

(3)

wherein,
$L^2$ and $Ar^2$ have the same meanings as $L^2$ and $Ar^2$ in the general formula (2), respectively;
$L^3$ represents a single bond or a divalent group selected from a substituted or unsubstituted aromatic hydrocarbon group, a substituted or unsubstituted aromatic heterocyclic group, or a linked aromatic group formed by linking two or three of aromatic rings of the substituted or unsubstituted aromatic hydrocarbon groups and the substituted or unsubstituted aromatic heterocyclic groups, the linked aromatic group may be linear or branched, and the aromatic rings to be linked may be identical to or different from each other;
Y represents B, N, P, or P=O; and
$Ar^3$'s each independently represent a substituted or unsubstituted aromatic hydrocarbon group or a substituted or unsubstituted aromatic heterocyclic group, and two $Ar^3$'s may be bonded to each other to form a fused heterocycle.

4. An organic electroluminescent device, comprising an organic layer containing the compound for an organic electroluminescent device of claim 1.

5. An organic electroluminescent device according to claim 4, wherein the organic layer containing the compound for an organic electroluminescent device is a light-emitting layer.

6. An organic electroluminescent device according to claim 5, wherein the light-emitting layer contains the compound for an organic electroluminescent device as a dopant material.

7. An organic electroluminescent device according to claim 5, wherein the light-emitting layer contains a phosphorescent light-emitting dopant and the compound for an organic electroluminescent device as a host material.

8. An organic electroluminescent device, comprising an organic layer containing compound for an organic electroluminescent device of claim 2.

9. An organic electroluminescent device, comprising an organic layer containing the compound for an organic electroluminescent device of claim 3.

10. An organic electroluminescent device according to claim 8, wherein the organic layer containing the compound for an organic electroluminescent device is a light-emitting layer.

11. An organic electroluminescent device according to claim 9, wherein the organic layer containing the compound for an organic electroluminescent device is a light-emitting layer.

* * * * *